US005405988A

United States Patent [19]

Klar et al.

[11] Patent Number: 5,405,988

[45] Date of Patent: Apr. 11, 1995

[54] 9-SUBSTITUTED BICYCLO[3.3.0]OCTANE DERIVATIVES, PROCESS FOR THEIR PRODUCTION AND THEIR PHARMACEUTICAL USE

[75] Inventors: Ulrich Klar; Helmut Vorbrüggen; Hartmut Rehwinkel; Karl Thierauch; Peter Verhallen, all of Berlin, Germany

[73] Assignee: Schering Aktiengesellschaft, Berlin, Germany

[21] Appl. No.: 74,868

[22] PCT Filed: Oct. 9, 1992

[86] PCT No.: PCT/DE92/00865

§ 371 Date: Jun. 11, 1993

§ 102(e) Date: Jun. 11, 1993

[87] PCT Pub. No.: WO93/07118

PCT Pub. Date: Apr. 15, 1993

[30] Foreign Application Priority Data

Oct. 11, 1991 [DE] Germany ........................ 41 34 156.2

[51] Int. Cl.[6] ............................................ C07C 307/02

[52] U.S. Cl. ...................................... 560/12; 562/430; 564/86; 564/87; 548/215; 548/250; 549/377

[58] Field of Search .......................... 562/430; 560/12; 564/86, 87; 548/215, 250; 549/377

[56] References Cited

U.S. PATENT DOCUMENTS

| | | | |
|---|---|---|---|
| 4,487,961 | 12/1984 | Aristoff | 562/501 |
| 4,588,823 | 5/1986 | Aristoff | 549/422 |
| 4,971,987 | 11/1990 | Vorbrueggen et al. | 514/374 |
| 5,053,400 | 10/1991 | Vorbruggen et al. | 514/150 |
| 5,162,353 | 11/1992 | Vorbrueggen et al. | 514/374 |

FOREIGN PATENT DOCUMENTS

| | | |
|---|---|---|
| 0086611 | 8/1983 | European Pat. Off. . |
| 0224275 | 6/1987 | European Pat. Off. . |
| 3428266 | 1/1986 | Germany . |
| 89/00990 | 2/1989 | WIPO . |

*Primary Examiner*—José G. Dees
*Assistant Examiner*—Joseph M. Conrad
*Attorney, Agent, or Firm*—Millen, White, Zelano & Branigan

[57] ABSTRACT

The invention relates to 9-substituted bicyclo[3.3.0]octane derivatives of formula I,

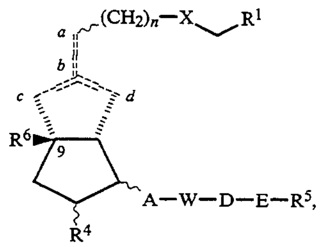

(I)

and their salts with physiologically compatible bases, as well as the $\alpha$-, $\beta$- or $\gamma$-cyclodextrin clathrates, as well as the compounds of formula I encapsulated with liposomes, process for their production and their pharmaceutical use.

22 Claims, No Drawings

9-SUBSTITUTED BICYCLO[3.3.0]OCTANE DERIVATIVES, PROCESS FOR THEIR PRODUCTION AND THEIR PHARMACEUTICAL USE

DESCRIPTION

The invention relates to 9-substituted bicyclo[3.3.0]octane derivatives, process for their production as well as their use as auxiliary agents for pharmacological studies and as pharmaceutical agents.

Bicyclo[3.3.0]octane derivatives have been intensively dealt with in recent years, since carbacyclins derived from the bicyclo[3.3.0]octane system, such as, e.g., iloprost or cicaprost or other analog isocarbacyclins, constitute biologically very potent as well as chemically and partially also metabolically stable prostacyclin-mimetic agents.

It has been found, surprisingly, that by the introduction of a suitable radical in 9-position (prostaglandin numbering system), chemically and metabolically stable carbacyclin analogs are obtained which, in addition, are able to antagonize the pharmacological properties of unstable thromboxane $A_2$ ($TXA_2$) or $PGH_2$ as well as its stable analogs, such as, e.g., U46619 or U44069.

The compounds of this invention therefore constitute valuable auxiliary agents for selective treatment of diseases which are attributable to a deficiency of endogenous $PGI_2$ and/or an excess of $TXA_2$ or $PGH_2$.

The invention relates to 9-substituted bicyclo[3.3.0]octane derivatives of formula I,

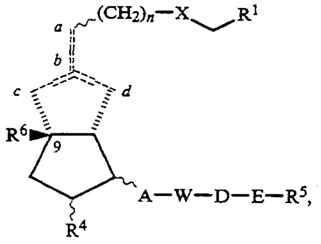

(I)

as well as their enantiomers, in which at most one double bond lies between the carbon atoms of centers a–b or b–c or b–d, $R^1$ can be

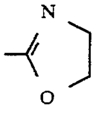, 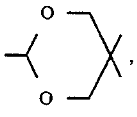, 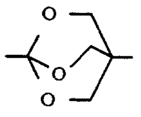,

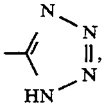, $COOR^2$, and $R^2$ can mean hydrogen or $C_1$–$C_{10}$ alkyl, $C_3$–$C_{10}$ cycloalkyl, $C_7$–$C_{16}$ aralkyl, optionally substituted by halogen, phenyl, $C_1$–$C_4$ alkoxy or di-($C_1$–$C_4$)-alkylamino, phenacyl or $C_6$–$C_{12}$ aryl substituted by Y or a 5- or 6-membered heterocyclic radical with at least one N, O or S atom, or —$CONHR^3$ with $R^3$ meaning hydrogen, $C_1$–$C_{10}$ alkanoyl or $C_1$–$C_{10}$ alkanesulfonyl, X means a $CH_2$ group, an oxygen atom or an O—$CH_2$—$CH_2$ group, n means 0 to 3, $R^4$ means a hydrogen atom, halogen, a free or functionally modified hydroxy group, and the OH group can be in α- or β-position, $R^6$ means —$(CH_2)_q$—$R^7$ or —C≡C—$(CH_2)_q$—$R^7$, q means 1 to 5, $R^7$ means

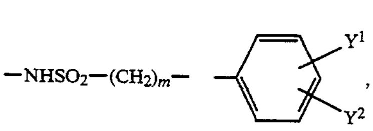, m means 0 to 2

A means a cis or trans CH═CH or a —C≡C group,

W means a

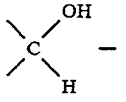 or 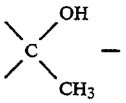

group, and the OH group can be in α- or β-position,

D and E together mean a bond or

D means a bond or $C_1$–$C_{10}$ alkylene,

E means a bond, a —C≡C group, a —$CR^9$═$CR^{10}$ group, and $R^9$ and $R^{10}$ are the same or different and mean hydrogen, chlorine or bromine, or a $C_1$–$C_5$ alkyl group or

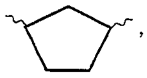, $R^5$ means a hydrogen atom, $C_1$–$C_{10}$ alkyl, $C_3$–$C_{10}$ cycloalkyl or $C_6$–$C_{12}$ aryl substituted by Y, $Y^1$ and $Y^2$ are the same or different and mean Y, Y means hydrogen, halogen, $N_3$, $NH_2$, CN, $CF_3$, $OR^8$, $NO_2$, $COOR^8$ or $C_1$–$C_{10}$ alkyl, $R^8$ can be hydrogen, $C_1$–$C_{10}$ alkyl, $C_6$–$C_{12}$ aryl or $C_7$–$C_{16}$ aralkyl optionally substituted by halogen and, if $R^2$ means hydrogen, their salts with physiologically compatible bases, as well as the α-, β- or γ-cyclodextrin clathrates, as well as the compounds of formula I encapsulated with liposomes.

The definition of 5- or 6-membered heterocyclic radical relates to heterocycles, which contain at least one heteroatom, preferably nitrogen, oxygen or sulfur. For example, there can be mentioned 2-furyl, 3-furyl, 2-thienyl, 3-thienyl, 2-pyridyl, 3-pyridyl, 4-pyridyl.

As alkyl groups $R^2$, $R^5$, $R^8$ and Y, straight-chain or branched-chain alkyl groups with 1–10 C atoms, such as, for example, methyl, ethyl, propyl, isopropyl, butyl, isobutyl, tert-butyl, pentyl, isopentyl, neopentyl, heptyl, hexyl, decyl, are suitable.

Alkyl groups R2, $R^5$, $R^8$ and Y can be substituted by halogen atoms, hydroxy groups, $C_1$14 $C_4$ alkoxy groups, $C_6$–$C_{12}$ aryl groups, which can be substituted by halogen, di-($C_1$–$C_4$)-alkylamines and tri-($C_1$–$C_4$)-alkylammonium. Those alkyl groups which are singly substituted are preferred.

As substituents, for example, there can be mentioned fluorine, chlorine or bromine atoms, phenyl, dimethylamino, diethylamino, methoxy, ethoxy.

As preferred alkyl groups $R^2$, $R^5$, $R^8$ and Y, those with 1-5 C atoms, such as, e.g., methyl, ethyl, propyl, isobutyl, butyl, chloroethyl, hydroxyethyl and 1- and 2-hydroxypropyl can be mentioned.

As alkylene groups D, straight-chain or branched-chain alkylene groups with 1-10 C atoms, such as, for example, methylene, ethylene, propylene, isopropylene, butylene, isobutylene, tert-butylene, pentylene, isopentylene, neopentylene, heptylene, hexylene, decylene, can be considered.

Alkylene groups D can be substituted by halogen atoms, hydroxy groups, $C_1$–$C_4$ alkoxy groups, $C_6$–$C_{12}$ aryl groups, which can be substituted by halogen, di-($C_1$–$C_4$)-alkylamines and tri-($C_1$–$C_4$)-alkylammonium. Those alkylene groups which are not substituted or are singly substituted are preferred.

As substituents, for example, there can be mentioned fluorine, chlorine or bromine atoms, phenyl, dimethylamino, diethylamino, methoxy, ethoxy.

As preferred alkylene groups D, those with 1-5 C atoms, such as, e.g., methylene, ethylene, propylene, isopropylene, isobutylene, butylene, chloroethylene, hydroxyethylene and 1- and 2-hydroxypropylene, can be mentioned.

As alkyl groups $R^9$ and $R^{10}$, methyl, ethyl, propyl isopropyl butyl, isobutyl, pentyl and isopentyl are suitable. Methyl and ethyl are preferred.

As aryl groups $R^2$, $R^5$ and $R^8$, for example, phenyl, diphenyl, 1-naphthyl and 2-naphthyl, which can be substituted by 1-3 halogen atoms, a phenyl group, 1-3 alkyl groups each with 1–4 C atoms, a chloromethyl group, fluoromethyl group, carboxyl group, $C_1$–$C_4$ alkoxy group or hydroxy group, are suitable.

The substitution in 3- and 4-position on the.phenyl ring is preferred, for example, by fluorine, chlorine, $C_1$–$C_4$ alkoxy or trifluoromethyl or in 4-position by hydroxy.

Cycloalkyl groups $R^2$ and $R^5$ can contain 3–10 carbon atoms, preferably 3–6 carbon atoms, in the ring. The rings can be substituted by alkyl groups with 1–4 carbon atoms. For example, there can be mentioned cyclopropyl, cyclobutyl, cyclopentyl, cyclohexyl, methylcyclopentyl, methylcyclohexyl.

The $C_7$–$C_{16}$ aralkyl groups in $R^2$ and $R^8$ can contain 6 to 14 C atoms, preferably 6 to 10 C atoms (phenyl or naphthyl), in the ring, and 1 to 4 C atoms, preferably 1 to 2 C atoms, in the alkyl chain. Preferred aralkyl radicals are, e.g., benzyl, phenylethyl, 1-phenylethyl, 1-(2)-naphthylmethyl or 1-(2)-naphthylethyl.

The hydroxy groups in $R^4$, Y and W can be functionally modified, for example, by etherification or esterification, and the free or modified hydroxy groups in $R^4$ and W can each be in $\alpha$-or $\beta$-position, and free hydroxy groups are preferred.

As ether and acyl radicals, the radicals known to one skilled in the art are suitable. Easily cleavable ether radicals, such as, for example, the tetrahydropyranyl, tetrahydrofuranyl, tert-butyldimethylsilyl, tert-butyldiphenylsilyl, tribenzylsilyl radical, are preferred. As acyl radicals, e.g., acetyl, propionyl, butyryl, benzoyl are suitable.

Halogen in the definitions for $R^2$, $R^4$, $R^8$ and Y means fluorine, chlorine, bromine and iodine.

Radicals "$C_1$–$C_{10}$ alkanoyl" or "$C_1$–$C_{10}$ alkanesulfonyl" for $R^3$ correspond to the already mentioned alkyl groups of the same length With the difference that they are bound on a carboxyl group. $C_1$–$C_4$ alkanoyl or $C_1$–$C_4$ alkanesulfonyl are preferred.

Inorganic and organic bases are suitable for salt formation with the free acids ($R^2$=H), as they are known to one skilled in the art for forming physiologically compatible salts. For example, there can be mentioned: alkali hydroxides, such as sodium hydroxide or potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)methylamine, etc.

The compounds of formula I in which $R^1$ means the groups $COOR^2$ or $CONHR^3$, $R^4$ means hydrogen, hydroxyl or halogen, $R^2$ means hydrogen or $C_7$–$C_{16}$ aralkyl, $C_5$–$C_6$ cycloalkyl, $C_1$–$C_{10}$ alkyl optionally substituted by halogen, $R^3$ means $C_1$–$C_7$ alkanoyl, $C_6$–$C_{12}$ arylsulfonyl, $C_1$–$C_7$ alkanesulfonyl, are preferred.

The compounds of formula I, in which $R^1$ means the groups $COOR^2$, $R^4$ means hydrogen or hydroxyl, $R^2$ means hydrogen or methyl, $R^3$ means methanesulfonyl, are especially preferred.

The invention further relates to a process for the production of 9-substituted bicyclo[3.3.0]octane derivatives of formula I, characterized in that the hydroxy compound of formula II is oxidized to an aldehyde of formula III and converted with a compound of formula IV to a compound of formula V,

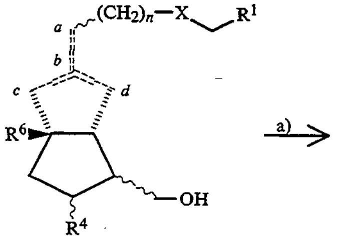

(II)

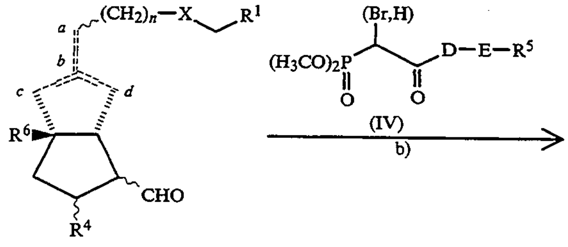

(IV)

(III)

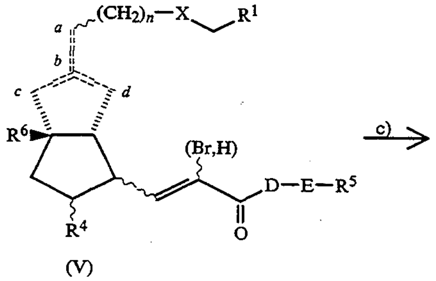

(V)

-continued

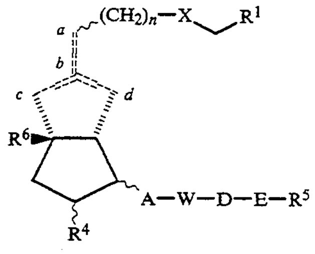

(I)

the formed ketone is reduced and hydrogen bromide optionally is eliminated, and a–b, b–c, b–d, $R^4$, $R^5$, $R^6$, A, W, D, E, n, X, $Y^1$, $Y^2$ and Hal have the above-indicated meanings and $R^1$ represents a —$COOR^2$-ester group with $R^2$ in the above-indicated meaning with the exception of hydrogen, is converted with physiologically compatible bases to their salts, reacted to a clathrate with α-, β- or γ-cyclodextrin or encapsulated with liposomes.

The reaction conditions of the above process steps are:

a) II→III

The oxidation of compounds of formula II to compounds of formula III takes place according to known processes, such as, e.g., according to that of Swern, Collins as well as with use of pyridinium dichromate or pyridinium chlorochromate in solvents such as dichloromethane, diethyl ether, tetrahydrofuran, benzene or toluene at −80° C. to −50° C. (Swern) or up to +30° (in the other oxidations) within 10 minutes to 8 hours.

b) III→V

The reaction of the compounds of formula III with compounds of formula IV to compounds of formula V takes place according to the process known to one skilled in the art in an inert solvent, such as, for example, dimethoxyethane with use of a deprotonating agent such as, e.g., sodium hydride at −50° C. to +50° C. (preferably at −10° C. to +25° C.) within 1 to 15 hours.

c) V→I

The reaction of compounds of formula V to compounds of formula I is performed with a reducing agent, such as, for example, sodium borohydride, in alcoholic (preferably methanolic) solution at −60° C. to −20° C. according to the process known to one skilled in the art. After the release of optionally protected hydroxyl groups, hydrogen bromide is optionally eliminated as described in example 5a.

The release of functionally modified hydroxy groups $R^4$, W and Y takes place according to the methods known to one skilled in the art. For example, the cleavage of ether protecting groups is performed in an aqueous solution of an organic acid, such as, e.g., acetic acid, propionic acid, citric acid, i.a, or in an aqueous solution of an inorganic acid, such as, e.g., hydrochloric acid, or in the case of tetrahydropyranyl ethers with use of pyridinium-p-toluenesulfonate, preferably in alcohols as solvent or with use of anhydrous magnesium bromide, preferably in diethyl ether as solvent.

To improve the solubility, a water-miscible inert solvent is suitably added with use of aqueous-acid reaction conditions. Proven as suitable, there are, e.g., alcohols, such as methanol and ethanol, ethers, such as dimethoxyethane, dioxane and tetrahydrofuran, whereby tetrahydrofuran is preferably used.

The cleavage of silylether protecting groups takes place, for example, with tetrabutylammonium fluoride according to the methods known to one skilled in the art. As solvents, for example, tetrahydrofuran, diethyl ether, dioxane, methylene chloride, etc., are suitable. The cleavage is performed preferably at temperatures between 20° C. and 80° C.

The saponification of the acyl groups and carbacyclin esters is performed according to the methods known to one skilled in the art, such as, for example, with basic catalysts, such as, e.g., with alkali or alkaline-earth carbonates or hydroxides in an alcohol or the aqueous solution of an alcohol. As alcohols, aliphatic alcohols, such as, e.g., methanol, ethanol, butanol, etc., but preferably methanol, are suitable. As alkali carbonates and hydroxides, there can be mentioned lithium, sodium and potassium salts. The lithium and potassium salts are preferred. As alkaline-earth carbonates and hydroxides, for example, calcium carbonate, calcium hydroxide and barium carbonate are suitable. The reaction generally takes place at −10° C. to +70° C., but preferably at +25° C.

The introduction of the ester group $CO_2R^2$ for $R^1$ or $CO_2R^8$ for Y, in which $R^2$ or $R^8$ represents an alkyl group with 1–10 C atoms, takes place according to the methods known to one skilled in the art. The carboxy compounds ($R^2$=H or $R^8$=H) are reacted, for example, with diazohydrocarbons in a way known in the art. The esterification with diazohydrocarbons takes place, e.g., in that a solution of the diazohydrocarbon in an inert solvent, preferably in diethyl ether, is mixed with the carboxy compound, dissolved in the same or in another likewise inert solvent, such as, e.g., methylene chloride. After completion of the reaction within 1 to 60 minutes, the solvent is removed and the ester is purified in the usual way. Diazoalkanes are either known or can be produced according to known methods [Org. Reactions, Vol. 8, pages 389–394 (1954)].

The introduction of the ester group $CO_2R^2$ for $R^1$ or $CO_2R^8$ for Y, in which $R^2$ or $R^8$ represents a substituted or unsubstituted aryl group, takes place according to the methods known to one skilled in the art. For example, the carboxy compounds are reacted with the corresponding arylhydroxy compounds with dicyclohexylcarbodiimide in the presence of a suitable base, such as, e.g., pyridine, DMAP, triethylamine, in an inert solvent, such as, e.g., methylene chloride, ethylene chloride, chloroform, ethyl acetate, tetrahydrofuran, but preferably with chloroform. The reaction is performed at temperatures between −30° C. and +50° C., preferably at +10° C.

The carbacyclin derivatives of formula I with $R^2$ or $R^8$ meaning a hydrogen atom can be converted to salts with suitable amounts of the corresponding inorganic bases with neutralization. For example, by dissolving the corresponding acids in water, which contains stoichiometric amounts of the base, the solid inorganic salt is obtained after evaporation of the water or after addition of a water-miscible solvent, e.g., alcohol or acetone.

The production of the amine salts takes place in the usual way. For this purpose, the acid is dissolved in a suitable solvent, such as, e.g., ethanol, acetone, diethyl ether or benzene and 1 to 5 equivalents of the respective amine is added to this solution. In this case, the salt usually accumulates in solid form or is isolated in the usual way after evaporation of the solvent.

The functional modification of the free hydroxy groups takes place according to the methods known to one skilled in the art. For the introduction of the ether protecting groups, it is reacted, for example, with dihydropyran or methyl vinyl ether in methylene chloride or chloroform with use of catalytic amounts of an acid condensing agent, such as, e.g., p-toluenesulfonic acid. The respective enol ether is added in excess, preferably in 1.2 to 10 times the amount of the theoretical requirement. The reaction normally takes place at −10° C. to +30° C. and is completed after 2 to 45 minutes.

For the introduction of silylether protecting groups, it is reacted, for example, with t-butyl-diphenylchlorosilane or t-butyl-dimethylchlorosilane in dimethylformamide with use of a base, such as, e.g., imidazole. The respective silyl chloride is added in excess, preferably in 1.05 to 4 times the amount of the theoretical requirement. The reaction normally takes place at 0° C. to 30° C. and is completed after 1 to 24 hours.

The introduction of the acyl protecting groups takes place by a compound of formula I being reacted in a way known in the art with a carboxylic acid derivative, such as, e.g., acid chloride, acid anhydride, etc.

The clathrates with α-, β- or γ-cyclodextrin are obtained analogously to the instructions in WO 87/05294. β-Cyclodextrin preferably is used.

Liposomes are produced according to the production process described in "Pharmazie in unserer Zeit [Pharmaceutics in Our Time ] 11, 98 (1982)."

All stereoisomeric forms also belong to the object of the invention.

BIOLOGICAL ACTION AND EXTENT OF APPLICABILITY OF THE NEW $TXA_2$ ANTAGONISTS

The compounds of this invention are suitable for treatment of diseases of the cardiovascular system, the stomach, the pancreas, the liver and the kidneys. They work in an antihypertensive and bronchodilatory manner. They are excellently suited for inhibition of the activation of platelets. Consequently, the new $TXA_2$ antagonists of formula I represent valuable pharmaceutical active ingredients. Moreover, the compounds are distinguished by a prostacyclin-mimetic active component, by higher selectivity, a substantially longer effectiveness and a greater stability as compared to similar $TXA_2$ antagonists.

The new $TXA_2$ antagonists have the properties typical for this family of compounds, such as, e.g., reduction of the peripheral-arterial, the coronary and pulmonary vascular resistance, reduction of the pulmonary blood pressure, reduction of the systemic blood pressure without reducing the cardiac output and coronary blood circulation at the same time, promotion of the kidney blood circulation and the blood circulation of other peripheral organs, increase of the cerebral blood circulation, inhibition of the platelet activation and dissolution of blood clots, inhibition of bronchoconstriction, inhibition of gastric acid secretion, cytoprotection of the heart, the stomach and intestinal mucous membrane, the liver, cytoprotection in the pancreas and in the kidneys as well as antiallergic properties. Therefore, the new $TXA_2$ antagonists are suitable on principle for treatment of stroke, prophylaxis and treatment of coronary heart diseases, for example, coronary thrombosis, for treatment of myocardial infarction, peripheral arteriopathies, for prophylaxis and treatment of other thromboembolic diseases and in arteriosclerosis, in ischemic attacks of the central nervous system and other disturbances of the blood circulation of the brain, such as, e.g., migraine, for treatment of hypertonia and for treatment of diseases which accompany an increase of the pulmonary vascular resistance, such as, e.g., the pulmonary hypertonia, and for treatment of shock, asthma and allergic rhinitis. They can further be used to inhibit labor pains and for treatment of toxicoses in pregnancies.

Further, the new $TXA_2$ antagonists can be used to improve the organ function after transplantation, for example, in kidney transplantation, to prevent rejection reactions, instead of heparin or as adjuvant in the case of dialysis or hemofiltration and in the case of storing dried blood plasma, for example, dried blood platelets.

The new $TXA_2$ antagonists have an antimetastatic action and antiproliferative properties. They are suitable on principle for treatment of neoplasias. The new $TXA_2$ antagonists can be used in combination with, for example, carbacyclins, prostacyclin and its analogs, 7-oxoprostacyclins, prostaglandins and their derivatives and 6-oxo-$PGE_1$- and 6-oxo-9-fluoroprostaglandin derivatives, with $TXA_2$-synthetase inhibitors, with phosphodiesterase inhibitors, with antagonists and receptor antagonists of various platelet stimulators (e.g., ADP, thrombin, collagen, PAF, adrenaline, serotonin, fibrinogen), with calcium antagonists, with fibrinolytic agents and thrombolytic agents, e.g., t-PA, streptokinase, with heparin and other anticoagulants, with cyclooxygenase inhibitors, e.g., acetylsalicylic acid, with inhibitors of lipoxygenases as well as antagonists of lipoxygenase products, with vasodilators, such as, e.g., nitro compounds, with antihypertensive agents, such as, e.g., β-blockers or with diuretics.

The dose of the compounds is 0.1–1000 mg/day, preferably 0.1–500 mg/day, also in several partial doses, if they are administered to human patients. The unit dose for the pharmaceutically acceptable vehicle is 0.1–100 mg. For parenteral administration, sterile, injectable aqueous or oily solutions are used. For oral administration, for example, tablets, coated tablets, or capsules are suitable.

Thus, the invention also relates to pharmaceutical agents based on the compounds of general formula I and usual auxiliary agents and vehicles.

The active ingredients according to the invention are to be used in connection with the auxiliary agents known and usual in galenicals, e.g., for the production of antihypertensive agents.

The unit dose range for the ampoule is 0.1–100 mg, for the tablet 0.1–100 mg.

EXAMPLE 1

5-[(3E/Z,1R,5R,6R,7R)-1-(4-Chlorophenylsulfonylaminomethyl)-6-[(1E,3S,4S)-3-hydroxy-4-methyl-1-nonen-6-inyl]-7-hydroxybicyclo[3.3.0]oct-3-ylidene]-pentanoic acid:

The solution of 58.3 mg (99 μmol) of compound A, represented according to example 1a, in 2.5 ml of methanol is mixed with 2 ml of a 5% lithium hydroxide solution and stirred for 2.5 hours at 23° C. By adding saturated citric acid, it is acidified, diluted with water and extracted several times with chloroform. It is washed with water, saturated sodium chloride solution and dried on magnesium sulfate. The residue obtained after filtration and removal of the solvent is purified by chromatography on 3 analytic thin-layer slabs. A mixture of dichloromethane and ethanol is used as mobile solvent, a mixture of chloroform and isopropanol is used as eluant. 53 mg (92 μmol, 93%) of the title compound is isolated as colorless oil.

$^1$H-NMR ($CDCl_3$): δ=0.92 (d,3H), 1.12 (t,3H), 1.38 (m, 1H), 1.6–2.4 (m,20H), 2.75 (d,2H), 3.5–5.0 (s,1H), 3.78 (m, 1H), 3.93 (m, 1H), 5.2 (m, 1H), 5.5 (m,2H), 5.96 (m, 1H), 7.48 (d,2H), 7.8 (d,2H) .

EXAMPLE 1a

5-[(3E/Z,1R,5R,6R,7R)-1-(4-Chlorophenylsulfonylaminomethyl)-6-[(1E,3S,4S)-3-hydroxy-4-methyl-1-nonen-6-inyl]-7-hydroxybicyclo[3.3.0]oct-3-ylidene]-pentanoic acid methyl ester (A) and 5-[(3E/Z,1R,5R,6R,7R)-1-(4-chlorophenylsulfonylaminomethyl)-6-[( 1E,3R,4S)-3-hydroxy-4-methyl-1-nonen-6-inyl]-7-hydroxybicyclo[3.3.0]oct-3-ylidene]-pentanoic acid methyl ester (B):

The solution of 160 mg (237 μmol) of the compound, represented according to example 1b, in 11 ml of anhydrous ethanol is mixed with a microspatula tip full of pyridinium-p-toluenesulfonate and heated under an atmosphere of dry argon for 2.5 hours to 55° C. It is concentrated by evaporation, taken up in dichloromethane and purified by chromatography on 7 analytic thin-layer slabs. Ethyl acetate is used as mobile solvent and eluant. 51.5 mg (87 μmol, 37%) of a nonpolar component, to which structure B is assigned, as well as 58.3 mg (99 mmol, 42%) of a polar component, to which structure A is assigned, are isolated.

IR (film) of A: 3600-3100, 3280, 3050, 2960, 2910, 2850, 1725, 1585, 1430, 1330, 1265, 1160, 1090, 1065, 1010, 970, 825, 735, 700 and 620 $cm^{-1}$.

IR (film) of B: 3600-3100, 3270, 3050, 2960, 2910, 2850, 1725, 1585, 1435, 1330, 1265, 1160, 1090, 1080, 1065, 1010, 970, 825, 750, 735, 700 and 615 $cm^{-1}$.

EXAMPLE 1b

5-[(3E/Z,1R,5R,6R,7R)-1-(4-Chlorophenylsulfonylaminomethyl)-6-[(1E,3RS,4S)-3-hydroxy-4-methyl-1-nonen-6-inyl]-7-(tetrahydropyran-2-yloxy)-bicyclo[3.3.-0]oct-3-ylidene]-pentanoic acid methyl ester:

The solution of 159 mg (235 μmol) of the compound represented according to example 1c is dissolved in 8.5 ml of anhydrous methanol, cooled under an atmosphere of dry argon to −50° C. and mixed in portions with a total of 22 mg of sodium borohydride. It is allowed to react for another 30 minutes, excess reducing agent is decomposed by adding 40 μl of acetone, mixed with water and extracted several times with diethyl ether. It is washed with water, saturated sodium chloride solution and dried on magnesium sulfate. The residue obtained after filtration and removal of the solvent of 160 mg (235 μmol, 100%) is further reacted without purification.

IR (film): 3600-3100, 3270, 3050, 2960, 2920, 2850, 1730, 1585, 1430, 1330, 1260, 1160, 1090, 1065, 1010, 970, 865, 825, 735, 700 and 620 $cm^{-1}$.

EXAMPLE 1c

5-[(3E/Z,1R,5R,6R,7R)-1-(4-Chlorophenylsulfonylaminomethyl)-6-[(1E,4S)-3-oxo-4-methyl-1-nonen-6-inyl]-7-(tetrahydropyran-2-yloxy)-bicyclo[3.3.-0]oct-3-ylidene]-pentanoic acid methyl ester:

The solution of 227 mg of dimethyl-(2-oxo-3S-methyl-oct-5-inyl)-phosphonate in 3 ml of anhydrous dimethoxyethane is instilled in the suspension of 25 mg of sodium hydride dispersion (80%) in 4 ml of anhydrous dimethoxyethane under an atmosphere of dry argon and stirred for 20 minutes at 23° C. Then, it is mixed with the solution of 440 mg (about 922 μmol) of the crude aldehyde, represented according to example 1d, in 4 ml of dichloromethane and stirred for 2 hours. After adding another 23 mg of sodium hydride dispersion, it is allowed to react for another hour, acidified by adding saturated citric acid, mixed with water and extracted several times with diethyl ether. The combined organic extracts are washed with water and saturated sodium chloride solution, dried on magnesium sulfate and the residue obtained after removal of the solvent is purified by chromatography on about 50 ml of fine silica gel with a gradient system of n-hexane and ethyl acetate. 159 mg (235 μmol, 31%) of the title compound is isolated as colorless oil.

$^1$H-NMR ($CDCl_3$): δ=1.08 (t,3H), 1.19 (d,3H), 1.35–1.75 (m,11H), 1.8–2.5 (m,14H), 2.75–3.0 (m,2H), 3.43 (m,1H), 3.67 (s,3H), 3.65–4.0 (m,2H), 4.48–4.6 (m, 1H), 5.02 (m, 1H), 5.21 (t,1H), 6.2 (2d, 1H), 6.78 (2dd,1H), 7.5 (d,2H), 7.79 (d,2H).

EXAMPLE 1d

5-[(3E/Z,1R,5R,6R,7R)-1-(4-Chlorophenylsulfonylaminomethyl)-6-formyl-7-(tetrahydropyran-2-yloxy)-bicyclo[3.3.0]oct-3ylidene]-pentanoic acid methyl ester:

The solution of 237 μl of dimethyl sulfoxide in 1 ml of dichloromethane is instilled in the solution of 130 μl of freshly distilled oxalyl chloride in 2.6 ml of anhydrous dichloromethane introduced under an atmosphere of dry argon at −70° C. allowed to react for 25 minutes and then mixed with the solution of 500 mg (899 μmol) of the alcohol, represented according to example 1e, in 3.1 ml of dichloromethane. It is allowed to react for 2.5 hours, mixed with 0.4 ml of triethylamine, poured in ice water and extracted several times with dichloromethane. The combined organic extracts are dried on magnesium sulfate. The residue, obtained after filtration and removal of the solvent, of 550 mg (maximum. 899 μmol) is further reacted without purification.

EXAMPLE 1e

5-[(3E/Z,1R,5R,6S,7R)-1-(4-Chlorophenylsulfonylaminomethyl)-6-hydroxymethyl-7-(tetrahydropyran-2-yloxy)-bicyclo[3.3.0]oct-3ylidene]-pentanoic acid methyl ester:

The solution of 1.56 g (1.96 mmol) of the compound, represented according to example 1f, in 30 ml of anhydrous tetrahydrofuran is mixed with 3.8 ml of a 1M solution of tetrabutylammonium fluoride in tetrahydrofuran and stirred for 1.5 hours at 23° C. under an atmosphere of dry argon, It is concentrated by evaporation and purified by chromatography on about 80 ml of fine silica gel with a gradient system of n-hexane and ethyl acetate. 1.08 g (1.94 mmol, 99%) of the title compound is isolated as colorless oil.

IR (film): 3600-3100, 3270, 3050, 2940, 2860, 1730, 1590, 1435, 1330, 1160, 1075, 1025, 865, 835, 750 and 735 $cm^{-1}$.

EXAMPLE 1f

5-[(3E/Z,1R,5R,6S,7R)-1-(4-Chlorophenylsulfonylaminomethyl)-6-(t-butyldiphenylsilyloxymethyl)-7-(tetrahydropyran-2-yloxy)bicyclo[3.3.0]oct-3-ylidene]-pentanoic acid methyl ester:

A total of 3 g of finely pulverized potassium-tert-butanolate is added to the emulsion of 5.64 g of carboxybutyltriphenylphosphonium bromide in 5 ml of anhydrous tetrahydrofuran and 12 ml of anhydrous dimethyl sulfoxide within one hour in portions. It is stirred until a clear red solution results, the solution of 1.61 g (2.31 mmol) of the compound, represented according to example 1g, in 5 ml of anhydrous tetrahydrofuran is rapidly instilled and allowed to react for 1.5 hours at 50° C. under an atmosphere of dry argon. It is poured in ice water, adjusted to a pH of 4–5 by adding a saturated citric acid solution and extracted several times with dichloromethane. It is washed with water and saturated sodium chloride solution, dried on magnesium sulfate, filtered and concentrated by evaporation. The obtained residue is taken up in dichloromethane, mixed at 3° C. with the ethereal solution of diazomethane, concentrated by evaporation after completion of the reaction and purified by chromatography on about 100 ml of fine silica gel with a gradient system of n-hexane and ethyl acetate. 1.56 g (1.96 mmol, 85%) of the title compound is isolated as colorless oil.

IR (film): 3270, 3060, 2940, 2850, 1730, 1585, 1425, 1330, 1160, 1110, 1025, 865, 820, 735 and 705 $cm^{-1}$.

EXAMPLE 1g (1S,5R,6S,7R)-1-(4-Chlorophenylsulfonylaminomethyl)-6-(t-butyldiphenylsilyloxymethyl)-7-(tetrahydropyran-2-yloxy)bicyclo[3.3.0]oct-3-one:

The solution of 1.66 g (2.38 mmol) of the compound, represented according to example 1f, in 80 ml of anhydrous dichloromethane is rapidly instilled in the red solution of 4 g of Collins reagent in 80 ml of anhydrous dichloromethane and stirred for 0.5 hours at 23° C. under an atmosphere of dry argon. It is filtered, rewashed well with dichloromethane, concentrated by evaporation and the residue is purified by chromatography on about 180 ml of fine silica gel with a gradient system of n-hexane and ethyl acetate. 1.56 g (2.22 mmol, 93%) of the title compound is isolated as colorless oil.

IR (film): 3270, 3050, 2940, .2860, 1735, 1585, 1470, 1425, 1335, 1265, 1160, 1110, 1090, 1020, 865, 820, 735 and 705 $cm^{-1}$.

EXAMPLE 1h (1R,3RS,5R,6S,7R)-1-(4-Chlorophenylsulfonylaminomethyl)-6- (t-butyldiphenylsilyloxymethyl)-7-(tetrahydropyran-2-yloxy)bicyclo[3.3.0]oct-3-ol:

The solution of 1.98 g (3.78 mmol) of the amino alcohol, represented according to example 1i, in 20 ml of anhydrous dichloromethane is mixed with 0.75 ml of triethylamine, 1.19 g of 4-chlorosulfonic acid chloride and stirred for 3 hours at 23° C. under an atmosphere of dry argon. It is concentrated by evaporation and purified by chromatography on about 80 ml of fine silica gel with a gradient system of n-hexane and ethyl acetate. 1.66 g (2.38 mmol, 64%) of the title compound is isolated as colorless oil.

IR (film): 3600-3100, 3270, 3060, 2940, 2850, 1585, 1470, 1425, 1330, 1260, 1160, 1110, 1080, 1020, 865, 825, 735 and 705 $cm^{-1}$.

EXAMPLE 1i (1R,3RS,5R,6S,7R)-1-Aminomethyl-6-(t-butyldiphenylsilyloxymethyl)-7-(tetrahydropyran-2-yloxy)-bicyclo[3.3.0]oct-3-ol:

The solution of 1.93 g (3.74 mmol) of the nitrile, represented according to example 1k, in 20 ml of diethyl ether is instilled in the suspension of 420 mg of lithium aluminum hydride in 35 ml of anhydrous diethyl ether within 30 minutes and stirred for 1 hour at 23° C. under an atmosphere of dry argon. Under ice cooling, it is mixed in succession with 5 ml of ethyl acetate, 420 μl of water, 420 μl of a 15% sodium hydroxide solution, 1.25 ml of water and stirred until a fine-grained precipitate results. It is suctioned off, rewashed with chloroform and concentrated by evaporation. 2.08 g (maximum. 3.74 mmol) of the title compound is isolated as colorless oil, which is further reacted without purification.

IR (film): 3600-3100, 3070, 3050, 2930, 2850, 1590, 1465, 1425, 1260, 1110, 1075, 1025, 865, 820, 735 and 705 $cm^{-1}$.

EXAMPLE 1k (1S,5R,6S,7R)-1-Cyano-6-(t-butyldiphenylsilyloxymethyl)-7-(tetrahydropyran-2-yloxy)-bicyclo[3.3.0]oct-3-one:

The solution of 2.45 g (4.99 mmol) of (5R,6S,7R)-7-(tetrahydropyran-2-yloxy)-6-tert-butyl-diphenylsilyloxymethylbicyclo[3.3.0]oct-1-en-3-one (representation see EP 0 358 290 A) in 30 ml of anhydrous toluene is mixed with 1.6 g of 18-crown 6, 655 mg of potassium cyanide, 550 μl of acetone cyanohydrin and stirred at 23° C. under an atmosphere of dry argon. It is poured on 100 ml of water, extracted several times with diethyl ether, the combined organic extracts are washed with water and saturated sodium chloride solution and dried on magnesium sulfate. The residue obtained after filtration and removal of the solvent is purified by chromatography on about 80 ml of fine silica gel with a gradient system of n-hexane and ethyl acetate. 1.57 g (3.04 mmol, 61%) of the title compound is isolated as colorless oil.

IR (film): 3070, 3050, 2940, 2860, 2230, 1745, 1590, 1425, 1110, 1080, 1025, 870, 820, 740 and 705 $cm^{-1}$.

EXAMPLE 2

5-[(3E/Z,1R,5R,6R,7R)-1-(4-Chlorophenylsulfonylaminomethyl)-6-[(1E,3R,4S)-3-hydroxy-4-methyl-1-nonen-6-inyl]-7-hydroxybicyclo[3.3.0]oct-3-ylidene]-pentanoic acid:

51.5 mg (86 μmol) of compound B represented according to example 1a is saponified analogously to example 1 and, after working up and purification, 44 mg (77 μmol, 89%) of the title compound is isolated as colorless oil.

$^1$H-NMR ($CDCl_3$): δ=0.95 (d,3H), 1.1 (t,3H), 1.42 (m, 1H), 1.6–2.4 (m,20H), 2.75 (m,2H), 3.5–5.0 (s,1H), 3.82 (m,1H), 4.17 (m,1H), 5.2 (m,1H), 5.58 (m,2H), 5.88 (m,1H), 7.48 (d,2H), 7.8 (d,2H).

EXAMPLE 3

4-[(3E/Z,1R,5R,6R,7R)-1-(4-Chlorophenylsulfonylaminomethyl)-6-[(1E,3S,4S)-3-hydroxy-4-methyl-1-nonen-6-inyl]-7-hydroxybicyclo[3.3.0]oct-3-ylidene]-butanoic acid:

14.6 mg (25 μmol) of compound B represented according to example 3a is saponified analogously to example 1 and, after working up and purification, 13.8 mg (24 μmol, 97%) of the title compound is isolated as colorless oil.

$^1$H-NMR ($CD_3OD$): δ=0.92 (d,3H), 1.1 (t,3H), 1.38 (m, 1H), 1.66 (m,1H), 1.75–2.45 (m,15H), 2.75 (s,2H), 3.72 (m,1H), 3.9 (m,1H), 5.27 (m,1H), 5.48 (m,2H), 7.54 (d,2H), 7.82 (d,2H).

EXAMPLE 3a

4-[(3E/Z,1R,5R,6R,7R)-1-(4-Chlorophenylsulfonylaminomethyl)-6-[(1E,3R,4S)-3-hydroxy-4-methyl-1-nonen-y-inyl]-7-hydroxybicyclo[3.3.0]oct-3-ylidene]-butanoic acid methyl ester (A) and 4-[(3E/Z,1R,5R,6R, 7R)-1-(4-chlorophenylsulfonylaminomethyl)-6-[(1E,3S,4S)-3-hydroxy-4-methyl-1-nonen-6-inyl]-7-hydroxybicyclo[3.3.0]oct-3-ylidene]-butanoic acid methyl ester (B):

35 mg (53 μmol) of the compound represented according to example 3b is reacted analogously to example 1a and, after working up and purification, 12.2 mg (21 μmol, 40%) of a nonpolar component, to which structure A is assigned, as well as 14.6 mg (25 μmol, 48%) of a polar component, to which structure B is assigned, is isolated in each case as colorless oil.

$^1$H-NMR ($CDCl_3$) of A: δ=0.94 (d,3H), 1.12 (t,3H), 1.45 (m,1H), 1.65–2.45 (m,16H), 2.78 (m,2H), 3.66 (s,3H), 3.82 (m, 1H), 3.97 (m, 1H), 5.18 (m, 1H), 5.4 (t,1H), 5.52 (m,2H), 7.5 (d,2H), 7.82 (d,2H).

$^1$H-NMR ($CDCl_3$) of B: δ=0.96 (d,3H), 1.12 (t,3H), 1.47 (m, 1H), 1.65–2.45 (m,16H), 2.79 (m,2H), 3.66 (s,3H), 3.82 (m, 1H), 4.19 (m, 1H), 5.17 (m, 1H), 5.25 (t,1H), 5.58 (m,2H), 7.5 (d,2H), 7.82 (d,2H).

EXAMPLE 3b

4-[(3E/Z,1R,5R,6R,7R)-1-(4-Chlorophenylsulfo nylaminomethyl)-6-[(1E,3RS,4S)-3-hydroxy-4-methyl-1-nonen-6-inyl]-7-(tetrahydropyran-2-yloxy)-bicyclo[3.3.0]oct-3-ylidene]-butanoic acid methyl ester:

40 mg (61 μmol) of the compound represented according to example 3c is reacted analogously to example 1b and, after working up and purification, 35 mg (53 μmol, 87%) of the title compound is isolated as colorless oil.

IR (film): 3600-3100, 3270, 3050, 2940, 2850, 1725, 1585, 1430, 1330, 1265, 1160, 1090, 1060, 1010, 970, 865, 825, 750, 735, 700 and 615 $cm^{-1}$.

EXAMPLE 3c

4-[(3E/Z,1R,5R,6R,7R)-1-(4-Chlorophenylsulfonylaminomethyl)-6-[(1E,4S)-3-oxo-4-methyl-1-nonen-6-inyl]-7-(tetrahydropyran-2-yloxy)-bicyclo[3.3.-0]oct-3-ylidene]-butanoic acid methyl ester:

189 mg (350 μmol) of the compound represented according to example 3d is reacted analogously to example 1d and, after working up and purification, 40 mg (61 μmol, 17%) of the title compound is isolated as colorless oil.

IR (film): 3270, 3050, 2940, 2870, 2850, 1730, 1690, 1660, 1620, 1585, 1435, 1335, 1265, 1160, 1075, 1030, 975, 865, 835, 750 and 735 $cm^{-1}$.

EXAMPLE 3d

4-[(3E/Z,1R,5R,6R,7R)-1-(4-Chlorophenylsulfonylaminomethyl)-6-formyl-7-(tetrahydropyran-2-yloxy)-bicyclo[3.3.0]oct-3ylidene]-butanoic acid methyl ester:

522 mg (963 μmol) of the compound represented according to example 3e is reacted analogously to example 1d and, after working up, 488 mg (904 μmol, 94%) of the title compound is isolated, which is further reacted without purification.

EXAMPLE 3e

4-[(3E/Z,1R,5R,6S,7R)-1-(4-Chlorophenylsulfonylaminomethyl)-6-hydroxymethyl-7-(tetrahydropyran-2-yloxy)-bicyclo[3.3.0]oct-3ylidene]-butanoic acid methyl esters:

828 mg (1.06 mmol) of the compound represented according to example 3f is reacted analogously to example 1e and, after working up and purification, 522 mg (963 μmol, 91%) of the title compound is isolated as colorless oil.

IR (film): 3600-3100, 3280, 3050, 2940, 2860, 1730, 1585, 1470, 1435, 1335, 1160, 1090, 1075, 1025, 975, 865, 825, 750 and 735 $cm^{-1}$.

EXAMPLE 3f

4-[(3E/Z,1R,5R,6S,7R)-1-(4-Chlorophenylsulfonylaminomethyl)-6-(t-butyldiphenylsilyloxymethyl)-7-(tetrahydropyran-2-yloxy)bicyclo[3.3.0]oct-3-ylidene]-butanoic acid methyl ester:

1.11 g (1.59 mmol) of the compound represented according to example 1g is reacted analogously to example if with use of carboxypropyltriphenylphosphonium bromide and, after working up, esterification and purification, 828 mg (1.06 mmol, 67%) of the title compound is isolated as colorless oil.

IR (film): 3270, 3050, 2940, 2850, 1730, 1585, 1425, 1330, 1160, 1110, 1025, 865, 815, 735 and 700 $cm^{-1}$.

EXAMPLE 4

4-[(3E/Z,1R,5R,6R,7R)-1-(4-Chlorophenylsulfonylaminomethyl)-6-[(1E,3R,4S)-3-hydroxy-4-methyl-1-nonen-6-inyl]-7-hydroxybicyclo[3.3.0]oct-3-ylidene]-butanoic acid:

12.2 mg (21 μmol) of compound A represented according to example 3a is saponified analogously to example 1 and, after working up and purification, 10.5 mg (19 μmol, 88%) of the title compound is isolated as colorless oil.

$^1$H-NMR ($CD_3OD$): δ=0.98 (d,3H), 1.1 (t,3H), 1.38 (m, 1H), 1.65 (m,1H), 1.8–2.4 (m,15H), 2.73 (s,2H), 3.72 (m,1H), 4.02 (m,1H), 5.25 (m,1H), 5.52 (m,2H), 7.58 (d,2H), 7.82 (d,2H).

EXAMPLE 5

5-[(3E/Z,1R,5R,6S,7R)-1-(4-Chlorophenylsulfonylaminomethyl)-6-[(3S,4S)-3-hydroxy-4-methyl-nona-1,6-diinyl]-7-hydroxybicyclo[3.3.0]oct-3-ylidene]-pentanoic acid:

100 mg (169 μmol) of the compound represented according to example 5a is saponified analogously to example 1 and, after working up and purification, 92 mg (159 μmol, 94%) of the title compound is isolated as colorless oil.

$^1$H-NMR ($CDCl_3$): δ=1.03 (d,3H), 1.12 (t,3H), 1.4 (m, 1H), 1.6–1.75 (m,2H), 1.88 (m,1H), 1.95–2.4 (m,16H), 2.77 (m,2H), 3.5–4.8 (s,1H), 4.02 (m,1H), 4.34 (m,1H), 5.23 (m,1H), 5.88 (m,1H), 7.49 (d,2H), 7.79 (d,2H).

EXAMPLE 5a

5-[(3E/Z,1R,5R,6S,7R)-1-(4-Chlorophenylsulfonylaminomethyl)-6-[(3S,4S)-3-hydroxy-4-methyl-nona-1,6-diinyl]-7-hydroxybicyclo[3.3.0]oct-3-ylidene]-pentanoic acid methyl ester:

The solution of 153 mg (228 μmol) of compound A represented according to example 5b in 7 ml of anhydrous toluene is mixed with 169 mg of 18-crown 6, 141 mg of cesium acetate and refluxed under an atmosphere of dry argon for 16 hours. It is purified by chromatography on 10 analytic thin-layer slabs. A mixture of n-hexane and ethyl acetate is used as mobile solvent, ethyl acetate is used as eluant. 100 mg (169 μmol, 74%) of the title compound is isolated as colorless oil.

$^1$H-NMR ($CDCl_3$): δ=1.06 (d,3H), 1.12 (t,3H), 1.45 (m, 1H), 1.6–1.75 (m,4H), 1.85–2.55 (m,16H), 2.82

(m,2H), 3.68 (s,3H), 4.08 (m,1H), 4.37 (m,1H), 5.22 (m,1H), 5.31 (m,1H), 7.5 (d,2H), 7.79 (d,2H).

EXAMPLE 5b

5-[(3E/Z,1R,5R,6S,7R)-1-(4-Chlorophenylsulfonylaminomethyl)-6-[(1Z,3S,4S)-2-bromo-3-hydroxy-4-methyl-non-1-en-6-inyl]-7-hydroxy-bicyclo[3.3.0]oct-3-ylidene]-pentanoic acid methyl ester (A) and 5-[(3E/Z,1R,5R,6S,7R)-1-(4-chlorophenylsulfonylaminomethyl)-6-[(1Z,3R,4S)-2-bromo-3-hydroxy-4-methyl-non-1-en-6-inyl]-7-hydroxy-bicyclo[3.3.0]oct-3-ylidene]pentanoic acid methyl ester (B):

406 mg (538 μmol) of the compound represented according to example 5c is reacted analogously to example 1a and, after working up and purification, 178 mg (265 μmol, 49%) of a nonpolar component, to which structure B is assigned, as well as 153 mg (228 μmol, 42%) of a polar component, to which structure A is assigned, are each isolated as colorless oil.

IR (film) of A and B: 3700-3100, 3280, 3050, 2950, 2870, 1725, 1585, 1430, 1330, 1260, 1160, 1090, 1010, 825, 735 and 700 $cm^{-1}$.

EXAMPLE 5c

5-[(3E/Z,1R,5R,6S,7R)-1-(4-Chlorophenylsulfonylaminomethyl)-6-[(1Z,3RS,4S)-2-bromo-3-hydroxy-4-methyl-non-1-en-6-inyl]-7-(tetrahydropyran-2-yloxy)-bicyclo[3.3.0]oct-3-ylidene]-pentanoic acid methyl ester:

592 mg (788 μmol) of the compound represented according to example 5d is reacted analogously to example 1b and, after working up and purification, 406 mg (538 μmol, 68%) of the title compound is isolated as colorless oil.

IR (film): 3600-3100, 3270, 3050, 2950, 2860, 1725, 1585, 1435, 1330, 1260, 1160, 1090, 1010, 870, 825, 735 and 700 $cm^{-1}$.

EXAMPLE 5d

5-[(3E/Z,1R,5R,6S,7R)-1-(4-Chlorophenylsulfonylaminomethyl)-6-[(1Z,4S)-2-bromo-3-oxo-4-methyl-non-1-en-6-inyl]-7-(tetrahydropyran-2-yloxy)-bicyclo[-3o3.01oct-3-ylidene]-pentanoic acid methyl ester:

The solution of 554 mg of dimethyl-(2-oxo-3S-methyl-oct-5-inyl)-phosphonate (which can be produced according to, e.g., Liebigs Ann. Chem. 1989, 1081–1083) in 5 ml of anhydrous dimethoxyethane is instilled in the suspension of 63 mg of sodium hydride dispersion (80%) in 8 ml of anhydrous dimethoxyethane at 3° C. under an atmosphere of dry argon. Then, it is mixed within 20 minutes in portions with a total of 422 mg of N-bromosuccinimide, allowed to react for another 30 minutes, the solution of 538 mg (971 μmol) of the crude aldehyde represented according to example 1d in 5 ml of anhydrous dimethoxyethane is rapidly instilled, allowed to heat to 23° C. and stirred for 6 hours. It is poured on a 10% ammonium chloride solution and extracted several times with diethyl ether. The combined organic extracts are washed with water, dried on magnesium sulfate and the residue obtained after removal of the solvent is purified by chromatography on about 50 ml of fine silica gel with a gradient system of n-hexane and ethyl acetate. 598 mg (794 μmol, 82%) of the title compound is isolated as colorless oil.

IR (film): 3270, 2940, 2870, 1735, 1680, 1610, 1585, 1450, 1435, 1335, 1250, 1160, 1070, 1030, 975, 870, 830 and 750 $cm^{-1}$.

EXAMPLE 6

5-[(3E/Z,1R,5R,6S,7R)-1-(4-Chlorophenylsulfonylaminomethyl)-6-[(3R,4S)-3-hydroxy-4-methyl-nona-1,6-diinyl]-7-hydroxybicyclo[3.3.0]oct-3-ylidene]-pentanoic acid:

106 mg (180 μmol) of the compound represented according to example 6a is saponified analogously to example 1 and, after working up and purification, 88 mg (153 μmol, 85%) of the title compound is isolated as colorless oil.

$^1$H-NMR ($CDCl_3$): δ=1.03 (d,3H), 1.12 (t,3H), 1.41 (m, 1H), 1.6–1.75 (m,2H), 1.88 (m,1H), 1.93–2.5 (m,16H), 2.77 (m,2H), 3.5–4.8 (s,1H), 4.02 (m,1H), 4.4 (m,1H), 5.22 (m, 1H), 5.88 (m,1H), 7.49 (d,2H), 7.79 (d,2H).

EXAMPLE 6a

5-[(3E/Z,1R,5R,6S,7R)-1-(4-Chlorophenylsulfonylaminomethyl)-6-[(3R,4S)-3-hydroxy-4-methyl-nona-1,6-diinyl]-7-hydroxybicyclo[3.3.0]oct-3-ylidene]-pentanoic acid methyl ester:

188 mg (280 μmol) of compound B represented according to example 5b is reacted analogously to example 5a and, after working up and purification, 106 mg (180 μmol, 70%) of the title compound is isolated as colorless oil.

$^1$H-NMR ($CDCl_3$): δ=1.05 (d,3H), 1.11 (t,3H), 1.45 (m,1H), 1.6–1.75 (m,4H), 1.85–2.55 (m,16H), 2.82 (m,2H), 3.68 (s,3H), 4.08 (m,1H), 4.42 (m,1H), 5.24 (m,2H), 7.5 (d,2H), 7.79 (d,2H).

EXAMPLE 7

4-[(3E/Z,1R,5R,6S,7R)-1-(4-Chlorophenylsulfonylaminomethyl)-6-[(3S,4S)-3-hydroxy-4-methyl-nona-1,6-diinyl]-7-hydroxybicyclo[3.3.0]oct-3-ylidene]-butanoic acid:

39 mg (68 μmol) of the compound represented according to example 7a is saponified analogously to example 1 and, after working up and purification, 34 mg (60 μmol, 89%) of the title compound is isolated as colorless oil.

$^1$H-NMR ($CD_3OD$): δ=1.03 (d,3H), 1.1 (t,3H), 1.78 (m,1H), 2.0–2.5 (m,15H), 2.73 (s,2H), 3.92 (m,1H), 4.3 (m,1H), 5.28 (m,1H), 7.58 (d,2H), 7.82 (d,2H).

EXAMPLE 7a

4-[(3E/Z,1R,5R,6S,7R)-1-(4-Ch! orophenylsulfonylaminomethyl)-6-[(3S,4S)-3-hydroxy-4-methyl-nona-,1,6-diinyl]-7-hydroxybicyclo[3.3.0]oct-3-ylidene]-butanoic acid methyl ester:

59 mg (90 μmol) of compound A represented according to example 7b is reacted analogously to example 5a and, after working up and purification, 39 mg (68 μmol, 76%) of the title compound is isolated as colorless oil.

$^1$H-NMR ($CDCl_3$): δ=1.05 (d,3H), 1.12 (t,3H), 1.49 (m, 1H), 1.89 (m,1H), 2.05–2.55 (m,15H), 2.7–2.85 (m, 4H), 3.66 (s,3H), 4.09 (m, 1H), 4.37 (m,1H), 5.19 (m, 1H), 5.36 (t,1H), 7.5 (d,2H), 7.82 (d,2H).

EXAMPLE 7b

4-[(3E/Z,1R,5R,6S,7R)-1-(4-Chlorophenylsulfonylaminomethyl)-6-[(1Z,3S,4S)-2-bromo-3-hydroxy-4-methyl-non-1-en-6-inyl]-7-hydroxy-bicyclo[3.3.0]oct-3-ylidene]-butanoic acid methyl ester (A) and 5-[(3E/Z,1R,5R,6S,7R)-1-(4-chlorophenylsulfonylaminomethyl)-6-[(1Z,3R,4S)-2-bromo-3-hydroxy-4-methyl-non-1-en-6-inyl]-7-hydroxy-bicyclo[3.3.0]oct-3-ylidene]butanoic acid methyl ester (B):

124 mg (187 μmol) of the compounds represented according to example 7c is reacted analogously to example 1a and, after working up and purification, 56 mg (85 μmol, 45%) of a nonpolar component, to which structure B is assigned, as well as 59 mg (90 μmol, 48%) of a polar component, to which structure A is assigned, is isolated in each case as colorless oil.

IR (film) of A and B: 3600-3100, 3270, 3050, 2960, 2860, 1725, 1590, 1430, 1330, 1260, 1160, 1090, 1010, 825, 735 and 700 $cm^{-1}$.

EXAMPLE 7c

4-[(3E/Z,1R,5R,6S,7R)-1-(4-Chlorophenylsulfonylaminomethyl)-6-[(1Z,3RS,4S)-2-bromo-3-hydroxy-4-methyl-non-1-en-6-inyl]-7-(tetrahydropyran-2-yloxy)-bicyclo[3.3.0]oct-3-ylidene]-butanoic acid methyl ester:

177 mg (239 μmol) of the compounds represented according to example 7d is reacted analogously to example 1b and, after working up and purification, 124 mg (187 μmol, 78%) of the title compound is isolated as colorless oil.

IR (film): 3600-3100, 3270, 3050, 2960, 2860, 1725, 1585, 1430, 1330, 1260, 1160, 1090, 1010, 865, 825, 735 and 700 $cm^{-1}$.

EXAMPLE 7d

4-[(3E/Z,1R,5R,6S,7R)-1-(4-Chlorophenylsulfonylaminomethyl)-6-[(1Z,4S)-2-brom-3-oxo-4-methyl-non-1-en-6-inyl]-7-(tetrahydropyran-2-yloxy)-bicyclo[3.3.0]oct-3-ylidene]-butanoic acid methyl ester:

191 mg (354 μmol) of the compound represented according to example 3d is reacted analogously to example 5d and, after working up and purification, 177 mg (239 μmol, 68%) of the title compound is isolated as colorless oil.

IR (film): 3270, 3080, 2930, 2870, 2850, 1735, 1685, 1610, 1585, 1440, 1335, 1240, 1160, 1035, 970, 865, 825 and 750 $cm^{-1}$.

EXAMPLE 8

4-[(3E/Z,1R,5R,6S,7R)-1-(4-Chlorophenylsulfonylaminomethyl)-6-[(3R,4S)-3-hydroxy-4-methyl-nona-1,6-diinyl]-7-hydroxybicyclo[3.3.0]oct-3-ylidene]-butanoic acid:

35 mg (61 μmol) of the compound represented according to example 8a is saponified analogously to example 1 and, after working up and purification, 29 mg (52 μmol, 76%) of the title compound is isolated as colorless oil.

$^1$H-NMR ($CD_3OD$): δ=1.03 (d,3H), 1.1 (t,3H), 1.76 (m, 1H), 2.0–2.5 (m,15H), 2.74 (s,2H), 3.92 (m, 1H), 4.3 (m, 1H), 5.28 (m, 1H), 7.57 (d,2H), 7.82 (d,2H).

EXAMPLE 8a

4-[(3E/Z,1R,5R,6S,7R)-1-(4-Chlorophenylsulfonylaminomethyl)-6-[(3R,4S)-3-hydroxy-4-methyl-nona-1,6-diinyl]-7-hydroxybicyclo[3.3.0]oct-3-ylidene]-butanoic acid methyl ester:

56 mg (85 μmol) of compound B represented according to example 7b is reacted analogously to example 5a and, after working up and purification, 35 mg (61.μmol, 71%) of the title compound is isolated as colorless oil.

$^1$H-NMR ($CDCl_3$): δ=1.05 (d,3H), 1.12 (t,3H), 1.49 (m,1H), 1.90 (m,1H), 2.05–2.55 (m,15H), 2.65–2.85 (m,4H), 3.66 (s,3H), 4.09 (m,1H), 4.42 (m, 1H), 5.19 (m, 1H), 5.32 (t,1H), 7.5 (d,2H), 7.82 (d,2H).

EXAMPLE 9

5-[(3E,1R,5R,6R,7R)-1-[5-Phenylsulfonylamino-1-pentinyl]-6-[(1E,3S,4RS)-3-hydroxy-4-methyl-oct-1-en-6-inyl]-7-hydroxybicyclo[3.3.0]oct-3-ylidene]-pentanoic acid:

16.7 mg (28 μmol) of the compound represented according to example 9a is saponified analogously to example 1 and, after working up and purification, 16.5 mg (28 μmol, 100%) of the title compound is isolated as colorless oil.

$^1$H-NMR ($CDCl_3$): δ=0.92 and 1.03 (in each case d, altogether 3H), 1.45–1.85 (m,10H), 1.95–2.55 (m,14H), 3.06 (m,2H), 3.5–4.5 (m, 5H), 5.05 (m,1H), 5.22 (m,1H), 5.53 (m,2H, 7.55 (m,3H), 7.87 (d,2H).

EXAMPLE 9a

5-[(3E,1R,5R,6R,7R)-1-[5-Phenylsulfonylamino-1-pentinyl]-6-[(1E,3S,4RS)-3-hydroxy-4-methyl-oct-1-en-6-inyl]-7-hydroxybicyclo[3.3.0]oct-3-ylidene]-pentanoic acid methyl ester:

22 mg (29 μmol) of the compound represented according to example 9b is reacted analogously to example 1a and, after working up and purification, 16.7 mg (28 μmol, 97%) of the title compound is isolated as colorless oil.

IR (film): 3260, 3050, 2940, 2850, 1725, 1435, 1330, 1160, 1125, 1075, 1020, 970, 900, 810, 73.5 and 695 $cm^{-1}$.

EXAMPLE 9b

5-[(3E,1R,5R,6R,7R)-1-[5-Phenylsulfonylamino-1-pentinyl]-6-[(1E,3S,4RS)-3-hydroxy-4-methyl-oct-1-en-6-inyl]-7-(tetrahydropyran-2-yloxy)-bicyclo[3.3.0]oct-3-ylidene]-pentanoic acid methyl ester:

30.7 mg (49 μmol) of the compound represented according to example 9c is reacted analogously to example 1h with use of benzenesulfonic acid chloride and, after working up and purification, 22 mg (29 μmol, 59%) of the title compound is isolated as colorless oil.

IR (film): 3270, 3050, 2940, 2860, 1730, 1440, 1330, 1160, 1130, 1075, 1020, 970, 900, 865, 810, 735 and 690 $cm^{-1}$.

EXAMPLE 9c

5-[(3E,1R,5R,6R,7R)-1-[5-Amino-1-pentinyl]-6-[(1E,3S,4RS)-3-hydroxy-4-methyl-oct-1-en-6-inyl]-7-(tetrahydropyran-2-yloxy)bicyclo[3.3.0]oct-3-ylidene]-pentanoic acid methyl ester:

116 mg (178 μmol) of 5-[(3E,1R,5R,6R,7R)-1-[5-azido-1pentinyl]-6-[(1E,3S,4RS)-3-hydroxy-4-methyl-oct-1-en-6-inyl]-7-(tetrahydropyran-2-yloxy)-bicyclo[3.3.0]oct-3-ylidene]-pentanoic acid methyl ester, which is produced as described in DE 3725031, is dissolved in 1.56 ml of anhydrous tetrahydrofuran, mixed with 56 mg of triphenylphosphine and stirred for 16 hours at 23° C. under an atmosphere of dry argon. Then, it is mixed with 0.31 ml of water and refluxed for 1 hour. It is concentrated by evaporation and purified by chromatography on 5 analytic thin-layer slabs. A mixture of n-hexane and acetone is used as mobile solvent, a mixture of acetone, chloroform and ethyl acetate is used as eluant. 88 mg (141 mg, 79%) of the title compound is isolated as colorless oil.

IR (film): 3600-3100, 2930, 2830, 1735, 1435, 1200, 1130, 1075, 1020, 970, 865, 815 and 735 $cm^{-1}$.

EXAMPLE 10

5-[(3E,1R,5R,6R,7R)-1-[5-(4-Methylphenylsulfonylamino)-1-pentinyl]-6-[(1E,3S,4RS)-3-hydroxy-4-methyl-oct-1-en-6-inyl]-7-hydroxy-bicyclo[3.3.0]oct-3-ylidene]-pentanoic acid:

19.5 mg (32 μmol) of the compound represented according to example 10a is saponified analogously to example 1 and, after working up and purification, 18.7 mg (31 μmol, 98%) of the title compound is isolated as colorless oil.

$^1$H-NMR ($CDCl_3$): δ=0.92 and 1.03 (in each case d, altogether 3H), 1.45–1.85 (m,10H), 1.9–2.55 (m,14H), 3.02 (m,2H), 3.5–4.6 (s,3H), 3.92 (m,1H), 4.03 (m,1H), 5.01 (m, 1H), 5.22 (m,1H), 5.53 (m,2H), 7.32 (d,2H), 7.75 (d,2H).

EXAMPLE 10a

5-[(3E,1R,5R,6R,7R)-1-[5-(4-Methylphenylsulfonylamino)-1-pentinyl]-6-[(1E,3S,4RS)-3-hydroxy-4-methyl-oct-1-en-6-inyl]-7-hydroxy-bicyclo[3.3.0]oct-3-ylidene]-pentanoic acid methyl ester:

29 mg (37 μmol) of the compound represented according to example 10b is reacted analogously to example 1a and, after working up and purification, 19.5 mg (32 μmol, 86%) of the title compound is isolated as colorless oil.

IR (film): 3600-3100, 3280, 3050, 2940, 2870, 1730, 1600, 1435, 1325, 1265, 1160, 1090, 970, 815, 735, 700 and 660 $cm^{-1}$.

EXAMPLE 10b

5-[(3E,1R,5R,6R,7R)-1-[5-(4-Methylphenylsulfonyla mino)-1-pentinyl]-6-[(1E,3S,4RS)-3-hydroxy-4-methyl-oct-1-en-6-inyl]-7-(tetrahydropyran-2-yloxy)-bicyclo[3.3.0]oct-3-ylidene]-pentanoic acid methyl ester:

24 mg (38 μmol) of the compound represented according to example 9c is reacted analogously to example lh with use of 4-methylbenzenesulfonic acid chloride and, after working up and purification, 29 mg (37 μmol, 97%) of the title compound is isolated as colorless oil.

IR (film): 3600-3100, 3270, 3050, 2940, 2860, 1730, 1600, 1435, 1325, 1260, 1160, 1090, 970, 865, 815, 735, 700 and 660 $cm^{-1}$.

EXAMPLE 11

5-[(3E,1R,5R,6R,7R)-1-[5-(4-Chlorophenylsulfonylamino)-1-pentinyl]6-[(1E,3S,4RS)-3-hydroxy-4-methyl-oct-1-en-6-inyl]-7-hydroxy-bicyclo[3.3.0]oct-3-ylidene]-pentanoic acid:

18.7 mg (30 μmol) of the compound represented according to example 11a is saponified analogously to example 1 and, after working up and purification, 16.4 mg (27 μmol, 89%) of the title compound is isolated as colorless oil.

$^1$H-NMR ($CDCl_3$): δ=0.92 and 1.03 (in each case d, altogether 3H), 1.45–1.85 (m,10H), 1.95–2.55 (m,14H), 3.07 (m,2H), 3.5–4.5 (m,5H), 5.12 (m,1H), 5.22 (m, 1H), 5.53 (m,2H), 7.5 (d,2H), 7.81 (d,2H).

EXAMPLE 11a

5-[(3E,1R,5R,6R,7R)-1-[5-(4-Chlorophenylsulfonylamino)-1-pentinyl]-6-[(1E,3S,4RS)-3-hydroxy-4-methyl-oct-1-en-6-inyl]-7-hydroxy-bicyclo[3.3.0]oct-3-ylidene]-pentanoic acid methyl ester:

25 mg (31 μmol) of the compound represented according to example 11b is reacted analogously to example 1a and, after working up and purification, 18.7 mg (30 μmol, 97%) of the title compound is isolated as colorless oil.

IR (film): 3270, 2940, 2860, 1730, 1585, 1435, 1330, 1160, 1120, 1080, 1015, 970, 815, 750 and 735 $cm^{-1}$.

EXAMPLE 11b

5-[(3E,1R,5R,6R,7R)-1-[5-(4-Chlorophenylsulfonyla mino)-1-pentinyl]-6-[(1E,3S,4RS)-3-hydroxy-4-methyl-oct-1-en-6-inyl]-7-(tetrahydropyran-2-yloxy)-bicyclo[3.3.0]oct-3-ylidene]-pentanoic acid methyl ester:

30.6 mg (49 μmol) of the compound represented according to example 9c is reacted analogously to example 1h and, after working up and purification, 25 mg (31 μmol, 63%) of the title compound is isolated as colorless oil.

IR (film): 3270, 2940, 2860, 1735, 1585, 1435, 1335, 1160, 1125, 1080, 1020, 970, 865, 815, 750 and 735 $cm^{-1}$.

EXAMPLE 12

5-[(3E,1R,5R,6R,7R)-1-[5-(4-Fluorophenylsulfonylamino)-1-pentinyl]-6-[(1E,3S,4RS)-3-hydroxy-4-methyl-oct-1-en-6-inyl]-7-hydroxy-bicyclo[3.3.0]oct-3-ylidene]-pentanoic acid:

16.5 mg (27 μmol) of the compound represented according to example 12a is saponified analogously to example 1 and, after working up and purification, 15 mg (25 μmol, 93%) of the title compound is isolated as colorless oil.

$^1$H-NMR ($CDCl_3$): δ=0.92 and 1.03 (in each case d, altogether 3H), 1.45–1.85 (m,10H), 1.95–2.55 (m, 14H), 3.05 (m,2H), 3.5–4.3 (m,5H), 5.12 (m,1H), 5.22 (m, 1H), 5.52 (m,2H), 7.20 (m, 2H), 7.88 (m,2H).

EXAMPLE 12a

5-[(3E,1R,5R,6R,7R) -1-[5-(4-Fluorophenylsulfonylamino)-1pentinyl-]-6-[(1E,3S,4RS)-3-hydroxy-4-methyl-oct-1-en-6-inyl]-7-hydroxy-bicyclo[3.3.0]oct-3-ylidene]-pentanoic acid methyl ester:

21 mg (27 μmol) of the compound represented according to example 12b is reacted analogously to example 1a and, after working up and purification, 16.5 mg (27 μmol, 100%) of the title compound is isolated as colorless oil.

EXAMPLE 12b

5-[(3E,1R,5R,6R,7R)-1-[5-(4-Fluorophenylsulfonylamino)-1-pentinyl-]-6-[(1E,3S,4RS)-3-hydroxy-4-methyl-oct-1-en-6-inyl]-7-(tetrahydropyran-2-yloxy)-bicyclo[3.3.0]oct-3-ylidene]-pentanoic acid methyl ester:

31 mg (50 μmol) of the compound represented according to example 9c is reacted analogously to example lh with use of 4-fluorobenzenesulfonic acid chloride and, after working up and purification, 21 mg (27 μmol, 54%) of the title compound is isolated as colorless oil.

EXAMPLE 13

5-[(3E,1S,5R,6R,7R)-1-[5-(4-Methylphenylsulfonylamino)-1-pentyl]-6-[(1E,3S,4RS)-3-hydroxy-4-methyl-oct-1-en-6-inyl]-7-hydroxy-bicyclo[3.3.0]oct-3-ylidene]-pentanoic acid:

15 mg (24 μmol) of the compound represented according to example 13a is saponified analogously to example 1 and, after working up and purification, 12.3 mg (21 μmol, 87%) of the title compound is isolated as colorless oil.

¹H-NMR (CD₃OD): δ=0.92 and 1.03 (in each case d, altogether 3H), 1.1–1.5 (m,11H), 1.55–2.5 (m,17H), 2.43 (s,3H), 3.07 (t,2H), 3.72 (m, 1H), 3.92 (m, 1H), 5.22 (m, 1H), 5.5 (m,2H), 7.38 (d,2H), 7.83 (d,2H).

EXAMPLE 13a

5-[(3E,1S,5R,6R,7R)-1-[5-(4-Methylphenylsulfonylamino)-1pentyl]-6-[(1E,3S,4RS)-3-hydroxy-4-methyl-oct-1-en-6-inyl]-7-hydroxy-bicyclo[3.3.0]oct-3-ylidene]-pentanoic acid methyl ester:

19.5 mg (25 μmol) of the compound represented according to example 13b is reacted analogously to example 1a and, after working up and purification, 15 mg (24 μmol, 98%) of the title compound is isolated as colorless oil.

IR (film): 3600–3100, 3050, 2920, 2850, 1730, 1670, 1600, 1535, 1440, 1340, 1260, 1160, 1090, 1010, 970, 890, 815, 735, 700 and 660 cm⁻¹.

EXAMPLE 13b

5-[(3E,1S,5R,6R,7R)-1-[5-(4-Methylphenylsulfonylamino)-1-pentyl]-6-[(1E,3S,4RS)-3-(tetrahydropyran-2-yloxy)-4-methyl-oct-1-en-6-inyl]-7-(tetrahydropyran-2-yloxy)-bicyclo[3.3.0]oct-3-ylidene]-pentanoic acid methyl ester:

23 mg (37 μmol) of the compound represented according to example 13c is reacted analogously to example 1h with use of 4-methylbenzenesulfonic acid chloride and, after working up and purification, 19.5 mg (25 μmol, 68%) of the title compound is isolated as colorless oil.

IR (film): 3340, 3050, 2930, 2850, 1735, 1665, 1540, 1450, 1340, 1255, 1200, 1160, 1125, 1075, 1020, 975, 865, 815, 735, 700 and 665 cm⁻¹.

EXAMPLE 13c

5-[(3E,1S,5R,6R,7R)-1-[5-Amino-1-pentyl]-6-[(1E,3S,4RS)-3-(tetrahydropyran-2-yloxy)-4-methyl-oct-1-en-6-inyl]-7-(tetrahydropyran-2-yloxy)-bicyclo[3.3.0]oct-3-ylidene]-pentanoic acid methyl ester:

26.4 mg (40 μmol) of 5-[(3E,1S,5R,6R,7R)-1-[5-azido-1Pentyl]-6-[(1E,3S,4RS)-3-(tetrahydropyran-2-yloxy)-4-methyl-oct-1-en-6-inyl]-7-(tetrahydropyran-2-yloxy)-bicyclo[3.3.0]oct-3ylidene]-pentanoic acid methyl ester, which is produced as described in DE 3742745 A1 and U.S. Pat. No. 4,971,987, is reacted analogously to example 9c and, after working up and purification, 23 mg (37 μmol, 91%) of the title compound is isolated as colorless oil.

IR (film): 3340, 2930, 2850, 1735, 1630, 1570, 1435, 1255, 1200, 1130, 1075, 1030, 1020, 975, 905, 865, 815, 735 and 700 cm⁻¹.

EXAMPLE 14

5-[(3E/Z,1R,5R,6R,7R)-1-(4-Chlorophenylsulfonylaminomethyl)-6-[(1E,3R or 3S)-3-hydroxy-oct-1-enyl ]-7-hydroxybicyclo[3.3.0 ]oct-3 -yl idene]-pentanoic acid:

11 mg (19 μmol) of the compound represented according to example 14a is saponified analogously to example 1 and, after working up and purification, 10.3 mg (18 μmol, 95%) of the title compound is isolated as colorless oil.

¹H-NMR (CDCl₃): δ=0.89 (t,3H), 1.20–1.60 (m,10H), 1.70 (m,3H), 1.90–2.1 (m,4H), 2.2–2.4 (m,5H), 2.75 (s,2H), 3.8 (m, 1H), 4.1 (m,1H), 4.2–4.5 (broad, 2H), 5.2 (s,1H), 5.6 (s,2H), 6.05 (s,broad,1H), 7.5 (d,2H), 7.8 (d,2H).

EXAMPLE 14a 5-(3E/Z,1R,5R,6R,7R)-1-(4-Chlorophenylsulfonylaminomethyl)-6-[(1E,3R or 3S)-3-hydroxy-oct-1-enyl]-7-hydroxybicyclo[3.3.0]oct-3-ylidene]-pentanoic acid methyl ester:

17.4 mg (27 μmol) of compound A represented according to example 14b is reacted analogously to example 1a and, after working up and purification, 11 mg (19 μmol, 70%) of the title compound is isolated as colorless oil.

IR (film): 3600-3100, 3053, 1725, 1595, 1500, 1330, 1260, 1095, 865, 740, 735 cm⁻¹.

EXAMPLE 14b

5-[(3E/Z,1R,5R,6R,7R)-1-(4-Chlorophenylsulfonylaminomethyl)-6-[(1E,3R or 3S)-3-hydroxy-oct-1-enyl]-7-(tetrahydropyran-2-yloxy)-bicyclo[3.3.0]oct-3-ylidene]-pentanoic acid methyl ester (A) and 5-[(3E/Z,1R,5R,6R,7R)-1-(4-chlorophenylsulfonylaminomethyl)-6-[(1E,3S or 3R)-3-hydroxy-oct-1-enyl]-7-(tetrahydropyran-2-yloxy)-bicyclo[3.3.0]oct-3-ylidene]pentanoic acid methyl ester (B):

55 mg (84 μmol) of the compound represented according to example 14c is reacted analogously to example 1b and, after working up and purification, 20.5 mg (31 μmol, 37%) of a nonpolar component, to which structure B is assigned, as well as 17.4 mg (27 μmol, 32%) of a polar component, to which structure A is assigned, is isolated in each case as colorless oil.

IR (film) of A and B: 3600-3100, 3260, 3000, 2970, 1720, 1595, 1420, 1330, 1250, 1165, 1080, 830, 735 and 700 cm⁻¹.

EXAMPLE 14c

5-[(3E/Z,1R,5R,6R,7R)-1-(4-Chlorophenylsulfonylaminomethyl)-6-[(1E)-3-oxo-oct-1-enyl]-7-(tetrahydropyran-2-yloxy)bicyclo[3.3.0]oct-3-ylidene]-pentanoic acid methyl ester:

56.6 mg of dimethyl-(2-oxo-heptyl)-phosphonate is added to the suspension of 7.4 mg of sodium hydride dispersion (80%) in 1.8 ml of anhydrous tetrahydrofuran under argon at room temperature. After completion of the gas generation, it is cooled to −30° C. and mixed with 113.9 mg of crude aldehyde, represented according to example 1d, dissolved in 0.7 ml of tetrahydrofuran. Then, it is allowed to react at a temperature between −25° C. and 2° C. for 3.5 hours. For working up, 0.11 ml of acetic acid is added, allowed to come to room temperature, diluted with diethyl ether, washed once with 10% ammonium chloride solution and three times with water. After drying the combined organic phases on magnesium sulfate and chromatography on silica gel with chloroform/diethyl ether in a ratio of 8/2, 55 mg (84 μmol, 41%) of the title compound is isolated.

IR (film): 3090, 3065, 3000, 2985, 1725, 1700, 1590, 1500, 1360, 1300, 1240, 1190, 1010, 835, 780 and 735 cm⁻¹.

EXAMPLE 15

5-[(3E/Z,1R,5R,6R,7R)-1-(4-Chlorophenylsulfonylaminomethyl)-6-[(1E,3S or 3R)-3-hydroxy-oct-1-enyl]-7-hydroxybicyclo[3.3.0]oct-3-ylidene]-pentanoic acid:

22.1 mg (38 μmol) of the compound represented according to example 15a is saponified analogously to example 1 and, after working up and purification, 18.1 mg (32 μmol, 84%) of the title compound is isolated as colorless oil.

$^1$H-NMR ($CDCl_3$): δ=0.9 (t,3H), 1.20–1.85 (m,13H), 1.85–2.15 (m,5H), 2.20–2.40 (m,4H), 2.75 (d,2H), 3.80 (q, 1H), 4.05 (m, 1H), 4.20–4.60 (broad,3H), 5.20 (s,1H), 5.50 (m,2H), 6.20 (s,1H), 7.49 (d,2H), 7.80 (d,2H).

EXAMPLE 15a

5-[(3E/Z,1R,5R,6R,7R)-1-(4-Chlorophenylsulfonylaminomethyl)-6-[(1E,3S or 3R)-3-hydroxy-oct-1-enyl]-7-hydroxybicyclo[3.3.0]oct-3-ylidene]-pentanoic acid methyl ester:

20.51 mg (31 μmol) of compound B represented according to example 14b is reacted analogously to example 1a and, after working up, 17 mg (33 μmol, 96%) of the title compound is isolated as colorless oil.

IR (film): 3600-3100, 3055, 1725, 1590, 1500, 1325, 1260, 1095, 860 and 735 $cm^{-1}$.

EXAMPLE 16

5-[(3E/Z,1R,5R,6R,7R)-1-(4-Chlorophenylsulfonylaminomethyl)-6-[(3R or 3S)-3-hydroxy-oct-1-inyl]-7-hydroxy-bicyclo[3.3.0]oct-3-ylidene]-pentanoic acid:

9.2 mg (16 μmol) of the compound represented according to example 16a is saponified analogously to example 1 and, after working up and purification, 7.4 mg (14 μmol, 88%) of the title compound is isolated as colorless oil.

$^1$H-NMR ($CDCl_3$): δ=0.90 (t,3H), 1.20–1.45 (m,7H), 1.60–1.80 (m,4H), 1.95–2.50 (m,11H), 2.80 (m,2H) , 4.0 (broad, 3H), 4.45 (t,1H), 5.20 (s,1H), 5.98 (s,1H), 7.50 (d,2H), 7.70 (d,2H).

EXAMPLE 16a

5-[(3E/Z,1R,5R,6R,7R)-1-(4-Chlorophenylsulfonylaminomethyl)-6-[(3R or 3S)-3-hydroxy-oct-1-inyl]-7-hydroxy-bicyclo[3.3.0]oct-3-ylidene]-pentanoic acid methyl ester:

13.7 mg (21 μmol) of the compound represented according to 16b is reacted analogously to example 5a and, after working up and purification, 9.2 mg (16 μmol, 76%) of the title compound is isolated as colorless oil.

IR (film): 3600-3120, 3010, 3000, 2970, 1725, 1590, 1495, 1380, 1320, 1250, 1200, 1160, 1080, 1000, 840, 735 and 700 $cm^{-1}$.

EXAMPLE 16b

5-[(3E/Z,1R,5R,6R,7R)-1-(4-Chlorophenylsulfonylaminomethyl)-6-[(1Z,3R or 3S)-2-bromo-3-hydroxy-oct-1-enyl]-7-hydroxybicyclo[3.3.0]oct-3-ylidene]-pentanoic acid methyl ester:

20.5 mg (28 μmol) of compound A represented according to 16c is reacted analogously to example la and, after working up and purification, 13.7 mg (21 μmol, 75%) of the title compound is isolated as colorless oil.

IR (film): 3650-3100, 3040, 3010, 3000, 2960, 1725, 1580, 1500, 1310, 1290, 1220, 1180, 1050, 1000, 870, 790 and 740 $cm^{-1}$.

EXAMPLE 16c

5-[(3E/Z,1R,5R,6R,7R)-1-(4-Chlorophenylsulfonylaminomethyl)-6-[(1Z,3R or 3S)-2-bromo-3-hydroxy-oct-1-enyl]-7-(tetrahydropyran-2-yloxy)-bicyclo[3.3.0]oct-3-ylidene]-pentanoic acid methyl ester (A) and 5-[(3E/Z,1R,5R,6R,7R)-1-( 4-chlorophenylsulfonylaminomethyl)-6-[(1Z,3S or 3R)-2-bromo-3-hydroxy-oct-1-enyl]-7-(tetrahydropyran-2-yloxy)bicyclo[3.3.0]oct-3-ylidene]-pentanoic acid methyl ester (B):

104 mg (142 μmol) of the compound represented according to example 16d is reacted analogously to example 1b and, after working up and purification, 34.3 mg (46 μmol, 32%) of a nonpolar component, to which structure B is assigned, as well as 20.5 mg (28 μmol, 20%) of a polar component, to which structure A is assigned, is isolated in each case as colorless oil.

IR (film) of A and B: 3600-3100, 3020, 3010, 3000, 2890, 1725, 1590, 1505, 1310, 1280, 1220, 1175, 1050, 1000, 870, 790 and 735 $cm^{-1}$.

EXAMPLE 16d

5-[(3E/Z,1R,5R,6R,7R)-1-(4-Chlorophenylsulfonylaminomethyl)-6-[(1Z)-2-brom-3-oxo-oct-1-enyl]-7-(tetrahydropyran-2-yloxy)bicyclo[3.3.0]oct-3-ylidene]-pentanoic acid methyl ester:

The solution of 67.7 mg of dimethyl-(2-oxo-heptyl)-phosphonate in 0.6 ml of anhydrous tetrahydrofuran is instilled in the suspension of 8.8 mg of sodium hydride dispersion (80%) in 1.9 ml of anhydrous tetrahydrofuran at room temperature under an atmosphere of dry argon and stirred for 10 minutes. Then, it is cooled to 0° C. and mixed with 57.8 mg of N-bromosuccinimide. It is allowed to react for one hour and. then 112.5 mg (203 μmol) of crude aldehyde, represented according to example 1d, dissolved in 0.7 ml of tetrahydrofuran, is instilled. It is allowed to heat to 23° C. stirred for 5 5 hours, then poured in 10% ammonium chloride solution and extracted several times with diethyl ether. The combined organic phases are washed with water, dried on magnesium sulfate and the residue obtained after removal of the solvent is purified by preparative slab chromatography with n-hexane/ethyl acetate in a ratio of 7/3 as eluant. 104 mg (143 μmol, 70%) of the title compound is isolated as colorless oil.

IR (film): 3280, 3010, 2940, 1725, 1680, 1610, 1595, 1465, 1330, 1250, 1160, 1000, 975, 840, 785 and 750 $cm^{-1}$.

EXAMPLE 17

5-[(3E/Z,1R,5R,6R,7R)-1-(4-Chlorophenylsulfonylaminomethyl)-6-[(3S or 3R)-3-hydroxy-oct-1-inyl]-7-hydroxy-bicyclo[3.3.0]oct-3-ylidene]-pentanoic acid:

15.4 mg (27 μmol) of the compound represented according to example 17a is saponified analogously to example 1 and, after working up and purification, 11.7 mg (21 μmol, 78%) of the title compound is isolated as colorless oil.

$^1$H-NMR ($CDCl_3$): δ=0.90 (t,3H), 1.20–1.50 (m,7H), 1.60–1.75 (m,4H), 1.95–2.45 (m,11H), 2.75 (s,2H), 4.0 (m,1H), 4.10–4.35 (broad,3H), 4.37 (t,1H), 5.25 (m, 1H), 6.05 (broad,1H), 7.50 (d,2H), 7.80 (d,2H).

EXAMPLE 17a

5-[(3E/z,1R,5R,6R,7R)-1-(4-Chlorophenylsulfonylaminomethyl)-6-[(3S or 3R)-3-hydroxy-oct-1-inyl]-7-hydroxy-bicyclo[3.3.0]oct-3-ylidene]-pentanoic acid methyl ester:

29 mg (45 μmol) of the compound represented according to 17b is reacted analogously to example 5a and, after working up and purification, 15.4 mg (27 μmol, 60%) of the title compound is isolated as colorless oil.

IR (film): 3600-3100, 3010, 3000, 2980, 1725, 1585, 1495, 1380, 1320, 1250, 1200, 1160, 1080, 1000, 840, 735 and 700 cm$^{31\ 1}$.

EXAMPLE 17b

5-[(3E/Z,1R,5R,6R,7R)-1-(4-Chlorophenylsulfonylaminomethyl)-6-[(1Z,3S or 3R)-2-bromo-3-hydroxy-oct-1-enyl]-7-hydroxybicyclo[3.3.0]oct-3-ylidene]-pentanoic acid methyl ester:

34.3 mg (47 μmol) of compound B represented according to 16c is reacted analogously to example 1a and, after working up and purification, 29 mg (45 μmol, 96%) of the title compound is isolated as colorless oil.

IR (film): 3600-3100, 3040, 3010, 3000, 2980, 1725, 1590, 1500, 1310, 1290, 1240, 1180, 1050, 1010, 870, 790 and 740 $cm^{-1}$.

EXAMPLE 18

5-[(3E/Z,1R,5R,6R,7R)-1-(4-Chlorophenylsulfonylaminomethyl)-6-[(1E,3R or 3S)-3-hydroxy-3-cyclohexyl-prop-1-enyl]-7-hydroxybicyclo[3.3.0]oct-3-ylidene]-pentanoic acid:

12.4 mg (21 μmol) of the compound represented according to example 18a is saponified analogously to example 1 and, after working up and purification, 10.3 mg (18 μmol, 85%) of the title compound is isolated as colorless oil.

$^1$H-NMR ($CDCl_3$): δ=0.9–1.05 (m,2H), 1.10–1.30 (m,3H), 1.30–1.50 (m,3H), 1.60–1.85 (m,8H), 1.90–2.1 (m,5H), 2.20–2.40 (m,5H), 2.75 (s,2H), 3.80 (s,2H), 4.10–4.50 (broad, 3H), 5.20 (s,1H), 5.55 (s,2H), 6.0 (broad, 1H), 7.50 (d,2H), 7.80 (d,2H).

EXAMPLE 18a

5-[(3E/Z,1R,5R,6R,7R)-1-(4-Chlorophenylsulfonylaminomethyl)-6-[(1E,3R or 3S)-3-hydroxy-3-cyclohexyl-prop-1-enyl]-7-hydroxybicyclo[3.3.0]oct-3-ylidene]-pentanoic acid methyl ester:

19.5 mg (29 μmol) of compound A represented according to 18b is reacted analogously to example 5a and, after working up and purification, 12.4 mg (21 μmol, 72%) of the title compound is isolated as colorless oil.

IR (film): 3600-3110, 3090, 3010, 2990, 2940, 1725, 1610, 1585, 1450, 1335, 1250, 1160, 1070, 1020, 975, 830 and 750 $cm^{-1}$.

EXAMPLE 18b

5-[(3E/Z,1R,5R,6R,7R)-1-(4-Chlorophenylsulfonylaminomethyl)-6-[(1E,3R or 3S)-3-hydroxy-3-cyclohexyl-prop-1-enyl]- 7-(tetrahydropyran-2-yloxy)-bicyclo[3.3.0]oct-3-ylidene]-pentanoic acid methyl ester (A) and 5-[(3E/Z,1R,5R,6R,7R)-1-(4-chlorophenylsulfonylaminomethyl)-6-[(1E,3S or 3R)-3-hydroxy-3-cyclohexyl-prop-1-enyl]-7-(tetrahydropyran-2-yloxy)-bicyclo[3.3.0]oct-3-ylidene]-pentanoic acid methyl ester (B):

72 mg (108 μmol) of the compound represented according to example 18c is reacted analogously to example 1b and, after working up and purification, 42.3 mg (64.μmol, 59%) of a nonpolar component, to which structure B is assigned, as well as 19.5 mg (29 μmol, 27%) of a polar component, to which structure A is assigned, is isolated in each case as colorless oil.

IR (film) of A and B: 3600-3100, 3020, 3000, 2980, 2970, 1735, 1600, 1460, 1435, 1360, 1310, 1280, 1220, 1110, 1020, 975, 870, 750 and 735 $cm^{-1}$.

EXAMPLE 18c

5-[(3E/Z,1R,5R,6R,7R)-1-(4-Chlorophenylsulfonylaminomethyl)-6-[(1E)-3-oxo-3-cyclohexyl-prop-1-enyl]-7-(tetrahydropyran-2-yloxy)-bicyclo[3.3.0]oct-3-ylidene]-pentanoic acid methyl ester:

60.4 mg of dimethyl-(2-oxo-2-cyclohexylethyl)-phosphonate is added to the suspension of 7.5 mg of sodium hydride dispersion (80%) in 1.9 ml of anhydrous tetrahydrofuran under argon at room temperature. After completion of the gas generation, it is cooled to −30° C. and mixed with 115.3 mg of crude aldehyde, represented according to example ld, dissolved in 0.7 ml of anhydrous tetrahydrofuran. Then, it is allowed to react at a temperature between −25° C. and 2° C. for 3.5 hours. For working up, 0.11 ml of acetic acid is added, allowed to come to room temperature, diluted with diethyl ether, washed once with 10% ammonium chloride solution and three times with water. After drying the combined organic extracts on magnesium sulfate and chromatography on silica gel with chloroform/diethyl ether in a ratio of 8/2 as eluant, 72 mg (109 μmol, 52%) of the title compound is isolated.

IR (film): 3080, 3070, 3010, 3000, 2985, 1730, 1700, 1590, 1495, 1350, 1310, 1260, 1180, 1120, 1030, 920, 835 and 770 $cm^{-1}$.

EXAMPLE 19

5-[(3E/Z,1R,5R,6R,7R)-1-(4-Chlorophenylsulfonylaminomethyl)-6-[(1E,3S or 3R)-3-hydroxy-3-cyclohexyl-prop-1-enyl]-7-hydroxybicyclo[3.3.0]oct-3-ylidene]-pentanoic acid:

28.9 mg (50 μmol) of the compound represented according to example 19a is saponified analogously to example 1 and, after working up and purification, 27 mg (48 μmol, 96%) of the title compound is isolated as colorless oil.

$^1$H-NMR ($CDCl_3$): δ=0.80–1.05 (m,2H), 1.10–1.45 (m,6H), 1.60–1.80 (m,6H), 1.80–2.15 (m,6H), 2.20–2.40 (m,5H), 2.75 (d,2H), 3.75 (m,2H), 4.30–4.70 (broad,3H), 5.15 (s,1H), 5.40–5.50 (m,2H), 6.05 (t,1H), 7.50 (d,H), 7.80 (d,2H).

EXAMPLE 19a

5-[(3E/Z,1R,5R,6R,7R)-1-(4-Chlorophenylsulfonylaminomethyl)-6-[(1E,3S or 3R)-3-hydroxy-3-cyclohexyl-prop-1-enyl]-7-hydroxybicyclo[3.3.0]oct-3-ylidene]-pentanoic acid methyl ester:

42 mg (63 μmol) of compound B represented according to 18b is reacted analogously to example 5a and, after working up and purification, 28.9 mg (50 μmol, 79%) of the title compound is isolated as colorless oil.

IR (film): 3600-3100, 3090, 3010, 2990, 2940, 1725, 1610, 1585, 1450, 1335, 1250, 1160, 1070, 1020, 975, 830 and 750 $cm^{-1}$.

EXAMPLE 20

5-[(3E/Z,1R,5R,6R,7R)-1-(4-Chlorophenylsulfonylaminomethyl)-6-[(3R or 3S)-3-hydroxy-3-cyclohexyl-prop-1-inyl]-7-hydroxybicyclo[3.3.0]oct-3-ylidene]-pentanoic acid:

19.1 mg (33 μmol) of the compound represented according to example 20a is saponified analogously to example 1 and, after working up and purification, 16,8 mg (30 μmol, 91%) of the title compound is isolated as colorless oil.

$^1$H-NMR ($CDCl_3$): δ=0.98–1.30 (m,5H), 1.35–1.60 (m,2H), 1.60–1.90 (m,7H), 1.95–2.50 (m,11H), 2.80

(s,2H), 4.05 (q, 1H), 4.15 (d,1H), 4.10–4.40 (broad,3H), 5.20 (s,1H), 5.90 (s,1H), 7.50 (d,2H), 7.80 (d,2H).

EXAMPLE 20a

5-[(3E/Z,1R,5R,6R,7R)-1-(4-Chlorophenylsulfonylaminomethyl)-6-[(3R or 3S)-3-hydroxy-3-cyclohexyl-prop-1-inyl]-7-hydroxybicyclo[3.3.0]oct-3-ylidene-pentanoic acid methyl ester:

21 mg (31 μmol) of the compound represented according to 20b is reacted analogously to example 5a and, after working up and purification, 18.1 mg (30 μmol, 97%) of the title compound is isolated as colorless oil.

IR (film); 3600-3100, 3020, 3010, 3000, 2890, 1720, 1600, 1495, 1440, 1360, 1320, 1260, 1240, 1190, 1130, 1050, 870 and 735 $cm^{-1}$.

EXAMPLE 20b

5-[(3E/Z,1R,5R,6R,7R)-1-(4-Chlorophenylsulfonylaminomethyl)-6-[(1Z,3R or 3S)-2-bromo-3-hydroxy-3-cyclohexyl-prop-1-enyl]-7-hydroxy-bicyclo[3.3.0]oct-3-ylidene]-pentanoic acid methyl ester:

29 mg (39 μmol) of compound A represented according to 20c is reacted analogously to example la and, after working up and purification, 21.2 mg (32 μmol, 82%) of the title compound is isolated as colorless oil.

IR (film): 3600-3090, 3040, 3010, 3000, 2980, 1725, 1595, 1495, 1310, 1280, 1220, 1180, 1050, 1020, 870, 790 and 740 $cm^{-1}$.

EXAMPLE 20c

5-[(3E/Z,1R,5R,6R,7R)-1-(4-Chlorophenylsulfonylaminomethyl)-6-[(1Z,3R or 3S)-2-bromo-3-hydroxy-3-cyclohexyl-prop-1-enyl]-7-(tetrahydropyran-2-yloxy)-bicyclo[3.3.0]oct-3-ylidene]-pentanoic acid methyl ester (A) and 5-[(3E/Z,1R,5R,6R,7R)-1-(4-chlorophenylsulfonylaminomethyl)-6-[(1Z,3S or 3R)-2-bromo-3-hydroxy-3-cyclohexyl-prop-1-enyl]-7-(tetrahydropyran-2-yloxy)bicyclo[3.3.0]oct-3-ylidene]-pentanoic acid methyl ester (B):

108 mg (145 μmol) of the compound represented according to example 20d is reacted analogously to example 1b and, after working up and purification, 51 mg (69 μmol, 48%) of a nonpolar component, to which structure B is assigned, as well as 29 mg (39 mol, 27%) of a polar component, to which structure A is assigned, is isolated in each case as colorless oil.

IR (film) of A and B: 3600-3100, 3020, 3010, 3000, 2880, 730, 1585, 1495, 1310, 1280, 1220, 1170, 1050, 1015, 870, 820, 790 and 735 $cm^{31\ 1}$.

EXAMPLE 20d

5-[(3E/Z,1R,5R,6R,7R)-1-(4-Chlorophenylsulfonylaminomethyl)-6-[(1Z)-2-brom-3-oxo-3-cyclohexyl-prop-1-enyl]-7-(tetrahydropyran-2-yloxy)-bicyclo[3.3.0]oct-3-ylidene]-pentanoic acid methyl ester:

The solution of 71.4 mg of dimethyl-(2-oxo-2-cyclohexylethyl)-phosphonate in 0.7 ml of anhydrous tetrahydrofuran is instilled in the suspension of 8.8 mg of sodium hydride dispersion (80%) in 1.9 ml of anhydrous tetrahydrofuran at room temperature under an atmosphere of dry argon and stirred for 10 minutes. Then, it is cooled to 0° C. and mixed with 57.8 mg of N-bromosuccinimide. It is allowed to react for one hour and then 112.6 mg (203 μmol) of crude aldehyde, represented according to example 1d, dissolved in 0.7 ml of tetrahydrofuran is instilled. It is allowed to heat to 23° C., stirred for 5.5 hours, then poured in 10% ammonium chloride solution and extracted several times with diethyl ether. The combined organic phases are washed with water, dried on magnesium sulfate and the residue obtained after removal of the solvent is purified by preparative slab chromatography with n-hexane/ethyl acetate in a ratio of 7/3 as eluate. 108 mg (146 μmol, 72%) of the title compound is isolated as colorless oil.

IR (film): 3290, 3010, 2950, 1725, 1685, 1610, 1595, 1465, 1325, 1250, 1160, 1010, 975, 840, 785 and 735 $cm^{-1}$.

EXAMPLE 21

5-[(3E/Z,1R,5R,6R,7R)-1-(4-Chlorophenylsulfonylaminomethyl)-6-[(3S or 3R)-3-hydroxy-3-cyclohexyl-prop-1-inyl]-7-hydroxybicyclo[3.3.0]oct-3-ylidene]-pentanoic acid:

36.2 mg (63 μmol) of the compound represented according to example 21a is saponified analogously to example 1 and, after working up and purification, 32.7 mg (58 μmol, 92%) of the title compound is isolated as colorless oil.

$^1$H-NMR ($CDCl_3$): δ=0.95–1.30 (m,5H), 1.35–1.55 (m,1H), 1.60–1.90 (m,7H), 1.95–2.50 (m,12H), 2.80 (d,2H), 4.05 (q,1H), 4.15 (d, 1H), 4.40–4.90 (broad,3H), 5.20 (1H), 5.95 (s,1H), 7.50 (d,2H), 7.80 (d,2H).

EXAMPLE 21a

5-[(3E/Z,1R,5R,6R,7R)-1-(4-Chlorophenylsulfonylaminomethyl)-6-[(3S or 3R)-3-hydroxy-3-cyclohexyl-prop-1-inyl]-7-hydroxybicyclo[3.3.0]oct-3-ylidene]-pentanoic acid methyl ester:

45.5 mg (69 μmol) of the compound represented according to 21b is reacted analogously to example 5a and, after working up and purification, 36.2 mg (63 μmol, 91%) of the title compound is isolated as colorless oil.

IR (film): 3600-3100, 3020, 3010, 3000, 2890, 1720, 1600, 1495, 1440, 1360, 1320, 1260, 1240, 1190, 1130, 1050, 870 and 735 $cm^{-1}$.

EXAMPLE 21b

5-[(3E/Z,1R,5R,6R,7R)-1-(4-Chlorophenylsulfonylaminomethyl)-6-[(1Z,3S or 3R)-2-bromo-3-hydroxy-3-cyclohexyl-prop-1-enyl]-7-hydroxy-bicyclo[3.3.0]oct-3-ylidene]-Pentanoic acid methyl ester:

51 mg (69 μmol) of compound B represented according to 20c is reacted analogously to example la and, after working up and purification, 45.5 mg (69 μmol, 100%) of the title compound is isolated as colorless oil.

IR (film): 3600-3090, 3040, 3010, 3000, 2980, 1725, 1595, 1495, 1310, 1280, 1220, 1180, 1050, 1020, 870, 790 and 740 $cm^{-1}$.

EXAMPLE 22

5-[(3E/Z,1R,5R,6R,7R)-1-(4-Chlorophenylsulfonylaminomethyl)-6-[(1E,3R or 3S,4RS)-3-hydroxy-4-phenyl-but-1-enyl]-7-hydroxybicyclo[3.3.0]oct-3-ylidene]-pentanoic acid:

14.7 mg (24 μmol) of the compound represented according to example 22a is saponified analogously to example 1 and, after working up and purification, 10.2 mg (17 μmol, 70%) of the title compound is isolated as colorless oil.

$^1$H-NMR ($CDCl_3$): δ=1.20 (d,3H), 1.35–1.45 (m,1H), 1.60–1.75 (m,3H), 1.90–2.15 (m,5H), 2.15–2.40 (m,5H), 2.70–2.85 (m,3H), 3.40–3.90 (broad,3H), 3.75 (q,1H), 4.15 (m,1H), 5.20 (s,1H), 5.55 (m,2H), 5.80 (s,1H), 7.15–7.35 (m,5H), 7.50 (d,2H), 7.75 (d,2H).

EXAMPLE 22a

5-[(3E/Z,1R,5R,6R,7R)-1-(4-Chlorophenylsulfonylaminomethyl)-6-[(1E,3R or 3S,4RS)-3-hydroxy-4-phenyl-but-1-enyl]-7-hydroxybicyclo[3.3.0]oct-3-ylidene]-pentanoic acid methyl ester:

22.4 mg (32 μmol) of compound A represented according to 22b is reacted analogously to example 5a and, after working up and purification, 14.7 mg (24 μmol, 75%) of the title compound is isolated as colorless oil.

IR (film): 3600-3100, 3090, 3010, 3000, 2990, 2980, 2940, 1725, 1610, 1585, 1450, 1335, 1250, 1150, 1110, 1070, 1030, 970, 830 and 735 $cm^{-1}$.

EXAMPLE 22b

5-[(3E/Z,1R,5R,6R,7R)-1-(4-Chlorophenylsulfonylaminomethyl)-6-[(1E,3R or 3S,4RS)-3-hydroxy-4-phenyl-but-1-enyl]-7-(tetrahydropyran-2-yloxy)-bicyclo[3.3.0]oct-3-ylidene]-pentanoic acid methyl ester (A) and 5-[(3E/Z,1R,5R,6R,7R)-1-(4-chlorophenylsulfonylaminomethyl)-6-[(1E,3S or 3R,4RS)-3-hydroxy-4-phenyl-but-1-enyl]-7-(tetrahydropyran-2-yloxy)bicyclo[3.3.0]oct-3-ylidene]-pentanoic acid ethyl ester (B):

83 mg (121 μmol) of the compound represented according to example 22c is reacted analogously to example 1b and, after working up and purification, 51.4 mg (75 μmol, 62%) of a nonpolar component, to which structure B is assigned, as well as 22.4 mg (33 μmol, 27%) of a polar component, to which structure A is assigned, is isolated in each case as colorless oil.

IR (film) of A and B: 3600-3100, 3060, 3000, 2990, 1725, 1595, 1450, 1330, 1250, 1165, 1080, 830, 740 and 700 $cm^{-1}$.

EXAMPLE 22c

5-[(3E/Z,1R,5R,6R,7R)-1-(4-Chlorophenylsulfonylaminomethyl)-6-[(1E,4RS)-3-oxo-4-phenyl-but-1-enyl]-7-(tetrahydropyran-2-yloxy)-bicyclo[3.3.0]oct-3-ylidene]-pentanoic acid methyl ester:

63.6 mg of dimethyl-(2-oxo-3RS-phenyl-propyl)-phosphonate is added to the suspension of 7.2 mg of sodium hydride dispersion (80%) in 1.8 ml of anhydrous tetrahydrofuran under argon at room temperature. After completion of the gas generation, it is cooled to −30° C. and mixed with 110.9 mg of crude aldehyde, represented according to example 1d, dissolved 0.7 ml of tetrahydrofuran. Then, it is allowed to react at a temperature between −25° C. and 2° C. for 3.5 hours. For working up, 0.11 ml of acetic acid is added, allowed to come to room temperature, diluted with diethyl ether, washed once with 10% ammonium chloride solution and three times with water. After drying the combined organic phases on magnesium sulfate and chromatography on silica gel with chloroform/diethyl ether in a ratio of 8/2, 83 mg (121 μmol, 61%) of the title compound is isolated.

IR (film): 3070, 3065, 3010, 3000, 2985, 1725, 1700, 1590, 1510, 1360, 1330, 1250, 1165, 1010, 835, 780, 735 and 700 $cm^{-1}$.

EXAMPLE 23

5-[(3E/Z,1R,5R,6R,7R)-1-(4-Chlorophenylsulfonylaminomethyl)-6-[(1E,3S or 3R,4RS)-3-hydroxy-4-phenyl-but-1-enyl]-7-hydroxybicyclo[3.3.0]oct-3-ylidene]-pentanoic acid:

40.2 mg (67 μmol) of the compound represented according to example 23a is saponified analogously to example 1 and, after working up and purification, 32.2 mg (55 μmol, 82%) of the title compound is isolated as colorless oil.

$^1$H-NMR ($CDCl_3$): δ=1.15 (d,3H), 1.25–1.40 (m, 1H), 1.60–1.80 (m,3H), 1.80–2.10 (m,5H), 2.10–2.35 (m,5H), 2.60–2.80 (m,3H), 3.70 (q, 1H), 3.95 (m, 1H), 4.20–4.60 (broad,3H), 5.20 (s,1H), 5.45 (m,2H), 6.00 (s,1H), 7.1 (t,1H), 7.15 (d,2H), 7.25 (m,2H), 7.50 (d,2H), 7.70 (d,2H).

EXAMPLE 23a

5-[(3E/Z,1R,5R,6R,7R)-1-(4-Chlorophenylsulfonylaminomethyl)-6-[(1E,3S or 3R,4RS)-3-hydroxy-4-phenyl-but-1-enyl]-7-hydroxybicyclo[3.3.0]oct-3-ylidene]-pentanoic acid methyl ester:

51.4 mg (75 μmol) of compound B represented according to 22b is reacted analogously to example 5a and, after working up and purification, 40.2 mg (66 μmol, 88%) of the title compound is isolated as colorless oil.

IR (film): 3600-3100, 3090, 3010, 3000, 2990, 2980, 2940, 1725, 1610, 1585, 1450, 1335, 1250, 1150, 1110, 1070, 1030, 970, 830 and 735 $cm^{-1}$.

EXAMPLE 24

5-[(3E/Z,1R,5R,6R,7R)-1-(4-Chlorophenylsulfonylaminomethyl)-6-[(1E,6E,3R or 3S,4RS)-3-hydroxy-4-methyl-7-chloro-oct-1,6-dien-1-yl]-7-hydroxy-bicyclo[3.3.0]oct-3-ylidene]-pentanoic acid:

15.4 mg (30 μmol) of the compound represented according to example 24a is saponified analogously to example 1 and, after working up and purification, 14.1 mg (23 μmol, 77%) of the title compound is isolated as colorless oil.

$^1$H-NMR ($CDCl_3$): δ=0.90 (t,3H), 1.45 (t,1H), 1.60–1.80 (m,4H), 1.90–2.10 (m,6H), 2.10 (s,3h), 2.20–2.40 (m,6H), 2.75 (d,2H), 3.50–4.00 (broad,3H), 3.75 (q, 1H), 4.00 (m, 1H), 5.20 (s,1H), 5.45 (t,1H), 5.60 (s,2H), 5.90 (s,1H), 7.50 (d,2H), 7.80 (d,2H).

EXAMPLE 24a

5-[(3E/Z,1R,5R,6R,7R)-1-(4-Chlorophenylsulfonylaminomethyl)-6-[(1E,6E,3R or 3S,4RS)-3-hydroxy-4-methyl-7-chloro-oct-1,6-dien-1-yl]-7-hydroxy-bicyclo[3.3.0]oct-3-ylidene]-pentanoic acid methyl ester:

21.6 mg (31 μmol) of compound A represented according to 24b is reacted analogously to example 5a and, after working up and purification, 15.4 mg (30 μmol, 97%) of the title compound is isolated as colorless oil.

IR (film): 3600-3100, 3010, 3000, 2990, 2980, 2940, 1725, 1585, 1450, 1340, 1260, 1210, 1150, 1110, 1070, 1030, 970, 940, 830 and 750 $cm^{-1}$.

EXAMPLE 24b

5-[(3E/Z,1R,5R,6R,7R)-1-(4-Chlorophenylsulfonylaminomethyl)-6-[(1E,6E,3R or 3S,4RS)-3-hydroxy-4-methyl-7-chloro-oct-1,6-dien-1-yl]-7-(tetrahydropyran-2-yloxy)-bicyclo[3-3.01oct-3-ylidene]-pentanoic acid methyl ester (A) and 5-[(3E/Z,1R,5R,6R,7R)-1-(4-chlorophenylsulfonylaminomethyl)-6-[(1E,6E,3S or 3R,4RS)-3-hydroxy-4-methyl-7-chloro-oct-1,6-dien-1-yl]-7-(tetrahydropyran-2-yloxy)-bicyclo[3.3.0]oct-3-ylidene]-pentanoic acid methyl ester (B):

71 mg (102 μmol) of the compound represented according to example 24c is reacted analogously to example lb and, after working up and purification, 45 mg (65 μmol, 64%) of a nonpolar component, to which structure B is assigned, as well as 21.6 mg (31 μmol, 30%) of a polar component, to which structure A is assigned, is isolated in each case as colorless oil.

IR (film) of A and B: 3600-3100, 3020, 3010, 3000, 2990, 1725, 1590, 1450, 1340, 1300, 1290, 1250, 1160, 1080, 830, 740 and 700 $cm^{-1}$.

EXAMPLE 24c

5-[(3E/Z,1R,5R,6R,7R)-1-(4-Chlorophenylsulfonyl aminomethyl)-6-[(1E,6E,4RS)-3-oxo-4-methyl-7-chloro-oct-1,6-dien-1-yl]-7-(tetrahydropyran-2-yloxy)-bicyclo[3.3.0]oct-3-ylidene]-pentanoic acid methyl ester:

66.1 mg of dimethyl-[(5E,3RS)-2-oxo-3-methyl-6-chloro-hept-5-en-1-yl]-phosphonate is added to the suspension of 7.1 mg of sodium hydride dispersion (80%) in 1.8 ml of anhydrous tetrahydrofuran under argon at room temperature. After completion of the gas generation, it is cooled to −30° C. and mixed with 110 mg of crude aldehyde, represented according to example 1d, dissolved in 0.7 ml of tetrahydrofuran. Then, it is allowed to react at a temperature between −20° C. and 7° C. for 3.5 hours. For working up, 0.11 ml of acetic acid is added, allowed to come to room temperature, diluted with diethyl ether, washed once with 10% ammonium chloride solution and three times with water. After drying the combined organic phases on magnesium sulfate and chromatography on silica gel with chloroform/diethyl ether in a ratio of 8/2, 71 mg (102 μmol, 51%) of the title compound is isolated.

IR (film): 3060, 3010, 3000, 2995, 1725, 1700, 1580, 1510, 1360, 1330, 1300, 1250, 1160, 1010, 835, 780, 740 and 700 $cm^{-1}$.

EXAMPLE 25

5-[(3E/Z,1R,5R,6R,7R)-1-(4-Chlorophenylsulfonylaminomethyl)-6-[(1E,6E,3S or 3R,4RS)-3-hydroxy-4-methyl-7-chloro-oct-1,6-dien-1-yl]-7-hydroxy-bicyclo[3.3.0]oct-3-ylidene]-pentanoic acid:

33.7 mg (44 μmol) of the compound represented according to example 25a is saponified analogously to example 1 and, after working up and purification, 26.7 mg (44 μmol, 68%) of the title compound is isolated as colorless oil.

$^1$H-NMR ($CDCl_3$): δ=0.90 (dd,3H), 1.40 (t,1H), 1.60–1.80 (m,4H), 1.85–2.10 (m,6H), 2.10 (s,3H), 2.20–2.35 (m,3H), 2.75 (d,2H), 3.80 (m,2H), 4.10–4.50 (broad,3H), 5.20 (s,1H), 5.50 (m,3H), 6.10 (s,1H), 7.50 (d,2H), 7.80 (d,2H).

EXAMPLE 25a

5-[(3E/Z,1R,5R,6R,7R)-1-(4-Chlorophenylsulfonylaminomethyl)-6-[(1E,6E,3S or 3R,4RS)-3-hydroxy-4-methyl-7-chloro-oct-1,6-dien-1-yl]-7-hydroxy-bicyclo[3.3.0]oct-3-ylidene]-pentanoic acid methyl ester:

45 mg (65 μmol) of compound B represented according to 24b is reacted analogously to example 5a and, after working up and purification, 33.7 mg (65 μmol, 100%) of the title compound is isolated as colorless oil.

IR (film): 3600-3100, 3010, 3000, 2990, 2980, 2940, 1725, 1585, 1450, 1340, 1260, 1210, 1150, 1110, 1070, 1030, 970, 940, 830 and 750 $cm^{-1}$.

EXAMPLE 26

5-[(3E/Z, 1R, 5R, 6R, 7R) -1- (4-Chlorophenylsulfonylaminomethyl)- 6-[(1E,3R or 3S) -3-hydroxy-5-phenyl-pent-1-enyl]-7-hydroxybicyclo[3.3.0]oct-3-ylidene]-pentanoic acid;

17 mg (28 μmol) of the compound represented according to example 26a is saponified analogously to example 1 and, after working up and purification, 15 mg (25 μmol, 89%) of the title compound is isolated as colorless oil.

$^1$H-NMR ($CDCl_3$): δ=1.40 (t,1H), 1.60–2.10 (m,10H), 2.20–2.35 (m,5H), 2.65 (m,2H), 2.75 (d,2H), 3.70 (q, 1H), 9.90–4.20 (broad,3H), 4.15 (m, 1H), 5.20 (s,1H), 5.60 (m,2H), 6.00 (s,1H), 7.15 (d,3H), 7.25 (m,2H), 7.45 (d,2H), 7.80 (d,2H).

EXAMPLE 26a

5-[(3E/Z,1R,5R,6R,7R)-1-(4-Chlorophenylsulfonylaminomethyl)-6-[(1E,3R or 3S)-3-hydroxy-5-phenyl-pent-1-enyl]-7-hydroxybicyclo[3.3.0]oct-3-ylidene]-pentanoic acid methyl ester:

20.5 mg (30 μmol) of compound A represented according to 26b is reacted analogously to example 5a and, after working up and purification, 17 mg (28 μmol, 93%) of the title compound is isolated as colorless oil.

IR (film): 3600-3100, 3010, 3000, 2990, 2970, 2940, 1720, 1585, 1440, 1340, 1240, 1210, 1180, 1150, 1110, 1060, 950, 940, 810 and 735 $cm^{-1}$.

EXAMPLE 26b

5-[(3E/Z,1R,5R,6R,7R)-1-(4-Chlorophenylsulfonylaminomethyl)-6-[(1E,3R or 3S)-3-hydroxy-5-phenyl-pent-1-enyl]-7-(tetrahydropyran-2-yloxy)-bicyclo[3.3.0]oct-3-ylidene]-pentanoic acid methyl ester (A) and 5-[(3E/Z,1R,5R,6R,7R)-1-(4-chlorophenylsulfonylaminomethyl)-6-[(1E,3S or 3R)-3-hydroxy-5- phenyl-pent-1-enyl]-7-(tetrahydropyran-2-yloxy)bicyclo[3.3.0]oct-3-ylidene]-pentanoic acid methyl ester (B):

71 mg (104 μmol) of the compound represented according to example 26c is reacted analogously to example 1b and, after working up and purification, 42 mg (61 μmol, 59%) of a nonpolar component, to which structure B is assigned, as well as 20.5 mg (30 μmol, 29%) of a polar component, to which structure A is assigned, is isolated in each case as colorless oil.

IR (film) of A and B: 3600-3100, 3020, 3010, 3000, 2990, 1725, 1580, 1480, 1340, 1310, 1290, 1230, 1160, 1080, 1050, 820, 740 and 730 $cm^{-1}$.

EXAMPLE 26c

5-[(3E/Z,1R,5R,6R,7R)-1-(4-Chlorophenylsulfonylaminomethyl)-6-[(1E)-3-oxo-5-phenyl-pent-1-enyl]-7-(tetrahydropyran-2-yloxy)bicyclo[3.3.0]-oct-3-ylidene]-pentanoic acid methyl ester:

65.4 mg of dimethyl-(2-oxo-4-phenyl-butyl)-phosphonate is added to the suspension of 7.4 mg of sodium hydride dispersion (80%) in 1.9 ml of anhydrous tetrahydrofuran is added under argon at room temperature. After completion of the gas generation, it is cooled to −30° C. and mixed with 114.1 mg of crude aldehyde, represented according to example ld, dissolved in 0.7 ml of tetrahydrofuran. Then, it is allowed to react at a temperature between −20° C. and 7° C. for 3.5 hours. For working up, 0.11 ml of acetic acid is added, allowed to come to room temperature, diluted with diethyl ether, washed once with 10% ammonium chloride solution and three times with water. After drying the combined organic phases on magnesium sulfate and chromatography on silica gel with chloroform/diethyl ether in a ratio of 8/2, 71.3 mg (104 μmol, 50%) of the title compound is isolated.

IR (film): 3050, 3020, 3010, 3000, 2990, 1725, 1700, 1590, 1490, 1330, 1310, 1300, 1250, 1180, 1160, 1000, 840, 760, 740 and 700 $cm^{-1}$.

EXAMPLE 27

5-[(3E/Z,1R,5R,6R,7R)-1-(4-Chlorophenylsulfonylaminomethyl)-6-[(1E,3S or 3R) -3-hydroxy-5-phenyl-pent-1-enyl]-7-hydroxybicyclo[3.3.0]oct-3-ylidene]-pentanoic acid:

27.8 mg (46 μmol) of the compound represented according to example 27a is saponified analogously to example 1 and, after working up and purification, 23.6 mg (40 μmol, 87%) of the title compound is isolated as colorless oil.

$^1$H-NMR ($CDCl_3$): δ=1.40 (m, 1H), 1.60–2.15 (m,10H), 2.20–2.35 (m,5H), 2.65 (m,2H), 2.75 (d,2H), 3.80 (q,1H), 4.10 (q, 1H), 4.15–4.50 (broad,3H), 5.20 (s,1H), 5.50 (m,2H), 6.10 (t,1H), 7.20 (d,3H), 7.25 (m,2H), 7.45 (d,2H), 7.80 (d,2H).

EXAMPLE 27a

5-[(3E/Z,1R,5R,6R,7R)-1-(4-Chlorophenylsulfonylaminomethyl)-6-[(1E,3S or 3R)-3-hydroxy-5-phenyl-pent-1-enyl]-7-hydroxybicyclo[3.3.0]oct-3-ylidene]-pentanoic acid methyl ester:

42 mg (61 μmol) of compound B represented according to 26b is reacted analogously to example 5a and, after working up and purification, 27.8 mg (46 μmol, 75%) of the title compound is isolated as colorless oil.

IR (film): 3600-3100, 3010, 3000, 2990, 2970, 2940, 1720, 1585, 1440, 1340, 1240, 1210, 1180, 1150, 1110, 1060, 950, 940, 810 and 735 $cm^{-1}$.

We claim:

1. A process for production of a bicyclo[3.3.0]octane compound of formula I

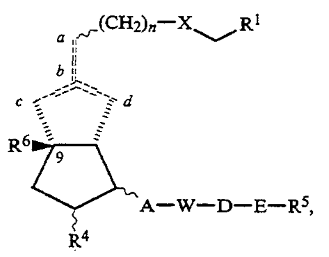

(I)

wherein at most one double bond lies between the carbon atoms at positions a–b, b–c or b–d;

$R^1$ is

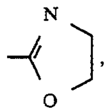, 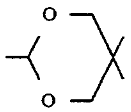, 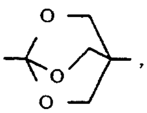,

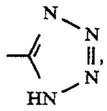, $COOR^2$ or $CONR^3$;

$R^2$ is hydrogen, $C_1$–$C_{10}$-alkyl, $C_3$–$C_{10}$-cycloalkyl, or $C_7$–$C_{16}$-aralkyl, in each case unsubstituted or substituted by halogen, phenyl, $C_1$–$C_4$-alkoxy or di-($C_1$–$C_4$)-alkylamino, phenacyl or $C_6$–$C_{12}$-aryl, in each case substituted by Y, or a 5- or 6-membered heterocyclic radical containing at least one N, O or S atom;

$R^3$ is hydrogen, $C_1$–$C_{10}$-alkanoyl or $C_1$–$C_{10}$-alkanesulfonyl;

X is $-CH_2-$, an oxygen atom or $-O-CH_2-CH_2-$;

n is 0 to 3;

$R^4$ is hydrogen, halogen, or a free or functionally modified hydroxy group in the α- or β-position;

$R^6$ is - $(CH_2)_q-R^7$ or $-C\equiv C-(CH_2)_q-R^7$;

q is 1 to 5;

$R^7$ is

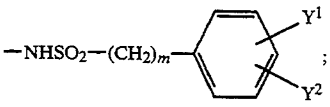;

m is 0 to 2;

A is a cis or trans $-CH=CH-$ or a $-C\equiv C-$;

W is a

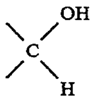 or 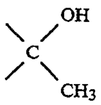

wherein OH can be in the α- or β-position;

D and E together are a bond or

D is a bond or $C_1$–$C_{10}$-alkylene, and

E is a bond, $-C\equiv C-$ or $-CR^9=CR^{10}-$;

$R^9$ and $R^{10}$ are, independently, hydrogen, chlorine, bromine, $C_1$–$C_5$-alkyl or

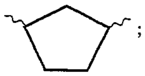;

$R^5$ is hydrogen or $C_1$–$C_{10}$-alkyl, $C_3$–$C_{10}$-cycloalkyl or $C_6$–$C_{12}$-aryl, in each case substituted by Y;

$Y^1$ and $Y^2$ are, independently, hydrogen, halogen, $N_3$, $NH_2$, CN, $CF_3$, $OR^8$, $NO_2$, $COOR^8$ or $C_1$–$C_{10}$-alkyl;

Y is hydrogen, halogen, $N_3$, $NH_2$, CN, $CF_3$, $OR^8$, $NO_2$, $COOR^8$ or $C_1$–$C_{10}$-alkyl; and $R^8$ is hydrogen or $C_1$–$C_{10}$-alkyl, $C_6$–$C_{12}$-aryl or $C_7$–$C_{16}$-aralkyl, in each case optionally substituted by halogen; or if $R^2$ is hydrogen, a salt thereof with a physiologically compatible base;

said process comprising:

oxidizing a compound of formula II

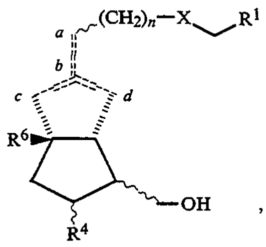

(II)

wherein a–b, b–c, b–d, $R^6$, n and X have the above-indicated meanings;

$R^1$ is —$COOR^2$, and $R^2$ is $C_1$–$C_{10}$-alkyl, $C_3$–$C_{10}$-cycloalkyl, or $C_7$–$C_{16}$-aralkyl, in each case unsubstituted or substituted by halogen, phenyl, $C_1$–$C_4$-alkoxy or di-($C_1$–$C_4$)-alkylamino, phenacyl or $C_6$–$C_{12}$-aryl, in each case substituted by Y, wherein Y is as defined above, or a 5- or 6-membered heterocyclic radical containing at least one N, O or S atom;

to an aldehyde of formula III

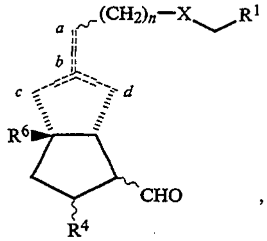

(III)

wherein a–b, b–c b–d, $R^1$, $R^4$, $R^6$, X and n have the above-indicated meanings, which is converted with a compound of formula IV

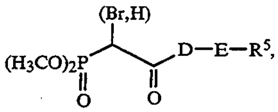

(IV)

wherein

D, E and $R^5$ have the above-mentioned meanings, to form a ketone compound of formula V,

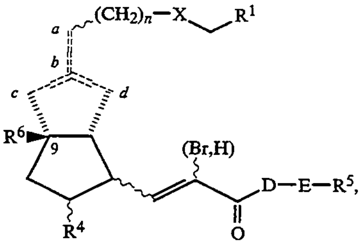

(V)

wherein a–b, b c, b–d, $R^6$, $R^4$, D, E, $R^5$, n and X have the above-indicated meanings, $R^1$ is —$COOR^2$, and $R^2$ is $C_1$–$C_{10}$-alkyl, $C_3$–$C_{10}$-cycloalkyl, or $C_7$–$C_{16}$-aralkyl, in each case unsubstituted or substituted by halogen, phenyl, $C_1$–$C_4$-alkoxy or di-($C_1$–$C_4$)-alkylamino, phenacyl or $C_6$–$C_{12}$-aryl, in each case substituted by Y, wherein Y is as defined above, or a 5- or 6-membered heterocyclic radical containing at least one N, O or S atom;

said ketone of formula V is reduced and hydrogen bromide optionally is eliminated, the obtained esters are saponified, converted with physiologically compatible bases to their salts, converted to a clathrate with α-, β- or γ-cyclodextrin or encapsulated with liposomes.

2. A 9-substituted bicyclo[3.3.0]octane compound of formula I,

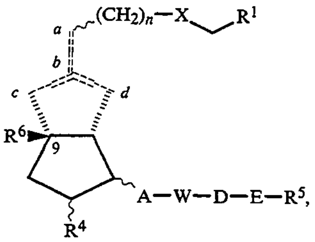

(I)

wherein at most one double bond lies between the carbon atoms at positions a–b, b–c or b–d;

$R^1$ is

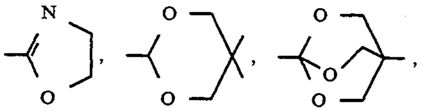

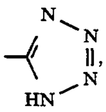

$COOR^2$ or $CONR^3$;

$R^2$ is hydrogen, $C_1$–$C_{10}$-alkyl, $C_3$–$C_{10}$-cycloalkyl, or $C_7$–$C_{16}$-aralkyl, in each case unsubstituted or substituted by halogen, phenyl, $C_1$–$C_4$-alkoxy or di-($C_1$–$C_4$)-alkylamino, phenacyl or $C_6$–$C_{12}$-aryl, in each case substituted by Y, or a 5- or 6-membered heterocyclic radical containing at least one N, O or S atom;

$R^3$ is hydrogen, $C_1$–$C_{10}$-alkanoyl or $C_1$–$C_{10}$-alkanesulfonyl;

X is —$CH_2$—, an oxygen atom or —O—$CH_2$—$CH_2$—;

n is 0 to 3;

$R^4$ is hydrogen, halogen, or a free or functionally modified hydroxy group in the α- or β-position;

$R^6$ is —$(CH_2)_q$—$R^7$ or —C≡C—$(CH_2)_q$—$R^7$;

q is 1 to 5;

$R^7$ is

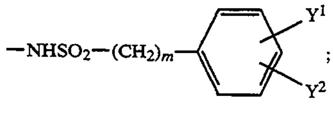

;

m is 0to 2;

A is a cis or trans —CH═CH— or a —C≡C—;

W is a

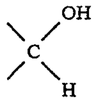

or

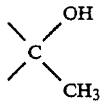

wherein OH can be in the α- or β-position;

D and E together are a bond or D is a bond or $C_1$–$C_{10}$-alkylene, and

E is a bond, —C≡C— or —$CR^9$═$CR^{10}$—;

$R^9$ and $R^{10}$ are, independently, hydrogen, chlorine, bromine, $C_1$–$C_5$-alkyl or

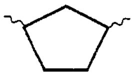

;

$R^5$ is hydrogen or $C_1$–$C_{10}$-alkyl, $C_3$–$C_{10}$-cycloalkyl or $C_6$–$C_{12}$aryl, in each case substituted by Y;

$Y^1$ and $Y^2$ are, independently, hydrogen, halogen, $N_3$, $NH_2$, CN, $CF_3$, $OR^8$, $NO_2$, $COOR^8$ or $C_1$–$C_{10}$-alkyl;

Y is hydrogen, halogen, $N_3$, $NH_2$, CN, $CF_3$, $OR^8$, $NO_2$, $COOR^8$ or $C_1$–$C_{10}$ - alkyl; and $R^8$ is hydrogen or $C_1$–$C_{10}$-alkyl, $C_6$–$C_{12}$-aryl or $C_7$–$C_{16}$-aralkyl, in each case optionally substituted by halogen; or if $R^2$ is hydrogen, a salt thereof with a physiologically compatible base.

3. A pharmaceutical composition comprising at least one compound of claim 2 and a pharmaceutically acceptable vehicle.

4. A composition according to claim 3, wherein the amount of said compounds is 0.1–100 mg.

5. A liposomal composition comprising at least one compound according to claim 2 encapsulated in at least one liposome.

6. A clathrate formulation comprising an α-, β- or γ-cyclodextrin clathrate of a compound according to claim 2.

7. A compound according to claim 2, wherein said 5- or 6-membered heterocyclic radical is 2-furyl, 3-furyl, 2-thienyl, 3-thienyl, 2-pyridyl, 3-pyridyl or 4-pyridyl.

8. A compound according to claim 2, wherein $R^2$ is $C_3$–$C_{10}$-cycloalkyl.

9. A compound according to claim 2, wherein $R^2$ is $C_3$–$C_{10}$-cycloalkyl.

10. A compound according to claim 2, wherein $R^9$ and $R^{10}$ are independently hydrogen, chlorine, bromine, methyl or ethyl.

11. A compound according to claim 2, wherein $R^1$ is $COOR^2$ or $CONHR^3$.

12. A compound according to claim 11, wherein $R^1$ is $CONHR^3$ and $R^3$ is methanesulfonyl.

13. A compound according to claim 11, wherein $R^1$ is $COOR^2$.

14. A compound according to claim 13, wherein $R^4$ is hydrogen or hydroxyl.

15. A compound according to claim 14, wherein $R^2$ is hydrogen or methyl.

16. A compound according to claim 2, wherein $R^4$ is hydrogen, hydroxyl or halogen.

17. A compound according to claim 16, wherein $R^2$ is hydrogen, $C_7$–$C_{16}$-aralkyl optionally substituted by halogen, $C_5$–$C_6$-cycloalkyl optionally substituted by halogen or $C_1$–$C_{10}$-alkyl optionally substituted by halogen.

18. A compound according to claim 17, wherein $R^3$ is $C_1$–$C_7$-alkanoyl, $C_6$–$C_{12}$-arylsulfonyl or $C_1$–$C_7$-alkanesulfonyl.

19. A 9-substituted bicyclo[3.3.0]octane compound of formula I,

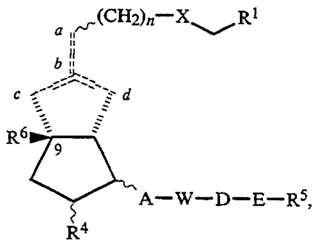

(I)

wherein at most one double bond lies between the carbon atoms at positions a-b, b-c or b-d;

$R^1$ is

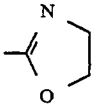

,

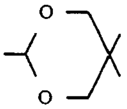

,

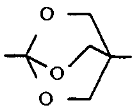

,

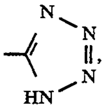

, $COOR^2$ or $CONR^3$;

$R^2$ is hydrogen, $C_1$–$C_{10}$-alkyl which is unsubstituted or substituted by halogen atoms, hydroxy groups, $C_1$–$C_4$-alkoxy groups, unsubstituted $C_6$–$C_{12}$2-aryl groups or $C_6$–$C_{12}$-aryl groups substituted by halogen, di-($C_1$–$C_4$)-alkylamine, or tri-($C_1$–$C_4$)-alkylammonium, $C_3$–$C_{10}$-cycloalkyl which is unsubstituted or substituted by $C_1$–$C_4$-alkyl groups, phenyl, diphenyl, 1-naphthyl, or 2-naphthyl which in each case are unsubstituted or substituted by 1-3 halogen atoms, phenyl, 1-3 $C_1$–$C_4$-alkyl, chloromethyl, fluoromethyl, carboxyl, $C_1$–$C_4$-alkoxy, or hydroxy, $C_7$–$C_{16}$-aralkyl containing 6-14 C atoms in the ring and 1-4 C atoms in the alkyl chain, or a 5- or 6-membered heterocyclic radical selected from 2-furyl, 3-furyl, 2-thienyl, 3-thienyl, 2-pyridyl, 3 -pyridyl, and 4 -pyridyl;

$R^3$ is hydrogen, $C_1$–$C_{10}$-alkanoyl or $C_1$–$C_{10}$-alkanesulfonyl;

X is —$CH_2$-, an oxygen atom or —O—$CH_2$—$CH_2$—;

n is 0 to 3;

$R^4$ is hydrogen, halogen, or a free or functionally modified hydroxy group in the α- or β-position;

$R^6$ is —$(CH_2)_q$—$R^7$ or —C≡C—$(CH_2)_q$—$R^7$;

q is 1 to 5;

$R^7$ is

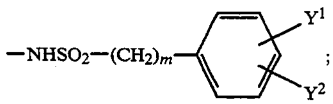

;

m is 0 to 2;

A is a cis or trans —CH═CH— or a —C≡C—;

W is a

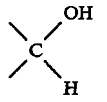

or

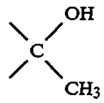

wherein OH can be in the α- or β-position;

D and E together are a bond or

D is a bond, unsubstituted $C_1$–$C_{10}$-alkylene, or $C_1$–$C_{10}$-alkylene substituted by halogen atoms, hydroxy groups, $C_1$–$C_4$-alkoxy groups, unsubstituted $C_6$–$C_{12}$-aryl groups, or $C_6$–$C_{12}$-aryl groups substituted by halogen, di-($C_1$–$C_4$)-alkylamines or tri-($C_1$–$C_4$)-alkylammonium; and E is a bond, —C≡C— or —$CR^9$═$CR^{10}$—;

$R^9$ and $R^{10}$ are, independently, hydrogen, chlorine, bromine, $C_1$–$C_5$-alkyl or

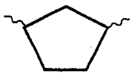

;

$R^5$ is hydrogen, $C_1$–$C_{10}$-alkyl which is unsubstituted or substituted by halogen atoms, hydroxy groups, $C_1$–$C_4$-alkoxy groups, unsubstituted $C_6$–$C_{12}$-aryl groups, or $C_6$–$C_{12}$-aryl groups substituted by halogen, di-($C_1$–$C_4$)-alkylamines, or tri-($C_1$–$C_4$)-alkylammonium, $C_3$–$C_{10}$-cycloalkyl which is unsubstituted or substituted by $C_1$–$C_4$-alkyl groups, or phenyl, diphenyl, 1-naphthyl, or 2-naphthyl which, in each case, are unsubstituted or substituted by 1-3 halogen atoms, phenyl, 1-3 $C_1$–$C_4$-alkyl groups, chloromethyl, fluoromethyl, carboxyl, $C_1$–$C_4$-alkoxy or hydroxy;

$Y^1$ and $Y^2$ are, independently, hydrogen, halogen, $N_3$, $NH_2$, CN, $CF_3$, $OR^8$, $NO_2$, $COOR^8$, unsubstituted $C_1$–$C_{10}$-alkyl, or $C_1$–$C_{10}$-alkyl substituted by halogen atoms, hydroxy groups, $C_1$–$C_4$-alkoxy groups, unsubstituted $C_6$–$C_{12}$-aryl groups, or $C_6$–$C_{12}$-aryl groups substituted by halogen, di-($C_1$–$C_4$)-alkylamines, or tri-($C_1$–$C_4$)-alkylammonium;

$R^8$ is hydrogen, $C_1$–$C_{10}$-alkyl which is unsubstituted or substituted by halogen atoms, hydroxy groups, $C_1$–$C_4$-alkoxy groups, unsubstituted $C_6$–$C_{12}$-aryl groups, or $C_6$–$C_{12}$-aryl groups substituted by halogen, di-($C_1$–$C_4$)-alkylamines or tri-($C_1$–$C_4$)-alkylammonium, phenyl, diphenyl, 1-naphthyl or 2-naphthyl, which in each case are unsubstituted or substituted by 1-3 halogen atoms, phenyl, 1-3 $C_1$–$C_4$-alkyl groups, chloromethyl, fluoromethyl, carboxyl, $C_1$–$C_4$-alkoxy or hydroxy, or $C_7$–$C_{16}$-aralkyl containing 6–14 C atoms in the ring and 1–4 atoms in the alkyl chain; or if $R^2$ is hydrogen, a salt thereof with a physiologically compatible base.

20. A pharmaceutical composition comprising at least one compound of claim 19 and a pharmaceutically acceptable vehicle.

21. A liposomal composition comprising at least one compound according to claim 19 encapsulated in at least one liposome.

22. A clathrate formulation comprising an α-, β- or γ-cyclodextrin clathrate of a compound according to claim 19.

* * * * *